(12) United States Patent
Kram et al.

(10) Patent No.: US 8,303,915 B2
(45) Date of Patent: Nov. 6, 2012

(54) THIN FILM APPARATUS AND METHOD

(75) Inventors: Brian H. Kram, Tucson, AZ (US);
Vincent R. Rizzo, Tucson, AZ (US);
Ryan Reeser, Tucson, AZ (US); David Chafin, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 1408 days.

(21) Appl. No.: 11/926,590

(22) Filed: Oct. 29, 2007

(65) Prior Publication Data

US 2008/0102006 A1 May 1, 2008

Related U.S. Application Data

(60) Provisional application No. 60/855,498, filed on Oct. 30, 2006.

(51) Int. Cl.
*G01N 1/31* (2006.01)
*G01N 35/02* (2006.01)
*B05C 5/02* (2006.01)

(52) U.S. Cl. ........ 422/563; 422/536; 422/501; 422/502; 422/503; 422/507; 422/300; 422/63; 422/65; 435/288.3; 118/323; 118/324; 118/500

(58) Field of Classification Search .............. 422/536, 422/63–67, 563, 501–503, 507, 68.1, 551, 422/300; 435/288.3; 118/323, 324, 500; 427/2.11

See application file for complete search history.

(56) References Cited

U.S. PATENT DOCUMENTS

| 3,431,886 | A | 3/1969 | McCormick et al. |
| 4,088,797 | A | 5/1978 | Johnson |
| 4,151,809 | A | 5/1979 | Johnson |
| 4,200,056 | A | 4/1980 | Johnson |
| 4,597,982 | A | 7/1986 | Delameter |
| 5,068,091 | A | 11/1991 | Toya |
| 5,578,452 | A | 11/1996 | Shi et al. |
| 5,675,715 | A * | 10/1997 | Bernstein et al. ............. 700/247 |
| 5,700,346 | A | 12/1997 | Edwards |
| 5,958,341 | A * | 9/1999 | Chu .............................. 422/536 |
| 5,985,669 | A | 11/1999 | Palander |
| 6,017,495 | A | 1/2000 | Ljungmann |
| 6,218,191 | B1 | 4/2001 | Palander |
| 6,793,890 | B2 * | 9/2004 | Morales et al. ............... 422/536 |
| 6,827,901 | B2 | 12/2004 | Copeland et al. |
| 2004/0002163 | A1 * | 1/2004 | Reinhardt et al. ............ 436/174 |
| 2005/0159982 | A1 | 7/2005 | Showalter et al. |
| 2005/0227298 | A1 | 10/2005 | Gourevitch |
| 2006/0171857 | A1 | 8/2006 | Stead et al. |
| 2007/0196909 | A1 | 8/2007 | Showalter et al. |

FOREIGN PATENT DOCUMENTS

| EP | 1 383 603 B1 | 8/2006 |
| EP | 1 691 184 A2 | 8/2006 |
| EP | 1 691 185 A1 | 8/2006 |
| WO | WO 97/03827 | 2/1997 |

* cited by examiner

*Primary Examiner* — Laura Edwards
(74) *Attorney, Agent, or Firm* — Ventana Medical Systems, Inc; Dawn M. Sims

(57) ABSTRACT

A platen for contacting a liquid to a surface of a substantially flat substrate is disclosed. The platen includes a liquid application station and a stripping element at an end of the liquid application station, wherein the stripping element includes an intersecting gap and an air barrier. Also disclosed are an apparatus including the platen and a method of using the platen to contact a substrate with a liquid.

25 Claims, 15 Drawing Sheets

THIN FILM APPARATUS AND METHOD

RELATED APPLICATION DATA

This claims the benefit of U.S. Provisional Application No. 60/855,498, filed Oct. 30, 2006, which application is incorporated by reference herein.

FIELD

The present invention relates to a platen-based apparatus and method for applying a liquid to a substantially flat substrate. More particularly, the present invention relates to an automated microscope slide staining apparatus and method that employ micro-fluidic featuring of a platen to enhance staining efficiency, increase staining flexibility and simplify waste management.

BACKGROUND

A wide variety of techniques that include placing a sample on a substrate have been developed to prepare and analyze biological samples. Examples of such techniques include microscopy, micro-array analyses (such as protein and nucleic acid micro-array analyses) and mass spectrometric methods such as MALDI and SELDI. In each of these techniques, preparation of samples for analysis can include contacting the sample on the substrate with one or more liquids. Where a sample is treated with multiple liquids, both application and subsequent removal of liquids can be important for providing a sample suitable for analysis.

In the context of microscope slides bearing biological samples (such as tissue sections or cells), the sample is typically treated with one or more dyes or conjugates of specific binding agents with detectable labels (such as nucleic acid probes and antibodies labeled with enzymes or fluorescent moieties) to add color and contrast to otherwise transparent or invisible cells or cell components. Historically, preparation of samples on microscope slides for analysis has included manual immersion of slides in containers of reagents. This labor intensive process suffers from a variety of shortcomings including inconsistency and carryover of reagents between containers, which leads to contamination and degradation of reagents.

Automation of the slide preparation process has helped to overcome the inherent inconsistency of the manual process, but many automated slide staining instruments simply try to replicate the manual process (see, for example, U.S. Pat. No. 6,017,495). While such "dip and dunk" type staining instruments increase throughput and consistency, they are not suited for more advanced staining protocols such as immunohistochemical (IHC) staining and in situ hybridization (ISH), especially because they do not eliminate reagent carryover between containers and generally do not provide adequate control over temperature.

Automated staining systems have been devised that are capable of advanced staining protocols such as IHC and ISH. Many of these systems apply liquids to a sample held on the top surface of a slide, and the liquid is either allowed to puddle over the sample (see, for example, U.S. Pat. No. 6,827,901) or is contained within a removable chamber that covers the top of the slide (see, for example, U.S. Pat. No. 6,218,191). Since IHC and ISH analyses are particularly sensitive to residual reagents left behind on a sample, these systems utilize repeated washing steps to remove residual reagents from the sample. Washing generates additional laboratory waste, adds expense to slide preparation and reduces throughput.

Another approach to applying liquids to substrates is illustrated by the platen-based systems described, for example, in U.S. Pat. Nos. 3,431,886, 4,200,056 and 5,700,346. These systems have found application in performing simple primary staining protocols such as hematoxylin and eosin (H&E) staining and Wright staining where significant residual reagent volumes left on a microscope slide between individual protocol steps can be tolerated. However, such systems were not designed for and do not appear capable of removing residual reagent volumes to an extent that permits more sophisticated staining protocols such as IHC and ISH. Furthermore, such systems do not incorporate a means for temperature control that is important for implementing advanced IHC and ISH protocols.

What is needed is an automated system that more effectively manages the application, and especially removal, of reagents from biological samples placed on substrates. Furthermore, a system that segregates different liquid wastes from multiple steps in a sample treatment process would be advantageous. A system that is configurable, flexible and can be easily adapted to perform multiple sample treatment protocols (such as primary and special staining protocols, IHC and ISH) also is desirable.

SUMMARY

In one aspect, a platen for contacting a liquid to a surface of a substantially flat substrate is disclosed. In one embodiment, the platen includes a liquid application station and a stripping element at an end of the liquid application station, wherein the stripping element includes an intersecting gap and an air barrier.

In another aspect, an apparatus is disclosed for contacting a liquid to a surface of a substantially flat substrate. In one embodiment, the apparatus includes a substrate transporter, a liquid applicator and a platen. The platen includes a liquid application station and a stripping element at an end of the station, wherein the stripping element includes an intersecting gap and an air barrier.

In yet another aspect, a method is disclosed for contacting a surface of a substantially flat substrate with a liquid. In one embodiment, the method includes introducing a liquid into a capillary space between the substrate and a liquid application station of a platen, and conveying the substrate past a stripping element of the platen, wherein the stripping element includes an intersecting gap and an air barrier and at least a portion of the liquid is removed through the intersecting gap.

In a further aspect, a sample conditioner is disclosed that includes a rotor having a plurality of recesses dimensioned to accommodate a substrate, a housing inside of which the rotor is rotated, a seal configured to contain pressure within the housing; and a source of pressure to pressurize the housing. A method for conditioning a sample also is disclosed that includes placing the substrate into a recess dimensioned to hold the substrate, where the recess is one of a plurality of such recesses formed in a rotor, rotating the rotor within a housing such that the substrate is moved past a seal and into an interior portion of a housing in which the rotor rotates, and subjecting the substrate to heat and pressure within the interior portion of the housing for a time sufficient to condition the sample (for example, retrieve antigens masked by fixation or nucleic acid targets masked by fixation). The method can further include contacting the sample with a sample conditioning solvent or solution within the interior portion of the housing.

DETAILED DESCRIPTION OF SEVERAL ILLUSTRATIVE EMBODIMENTS

Figure 1:
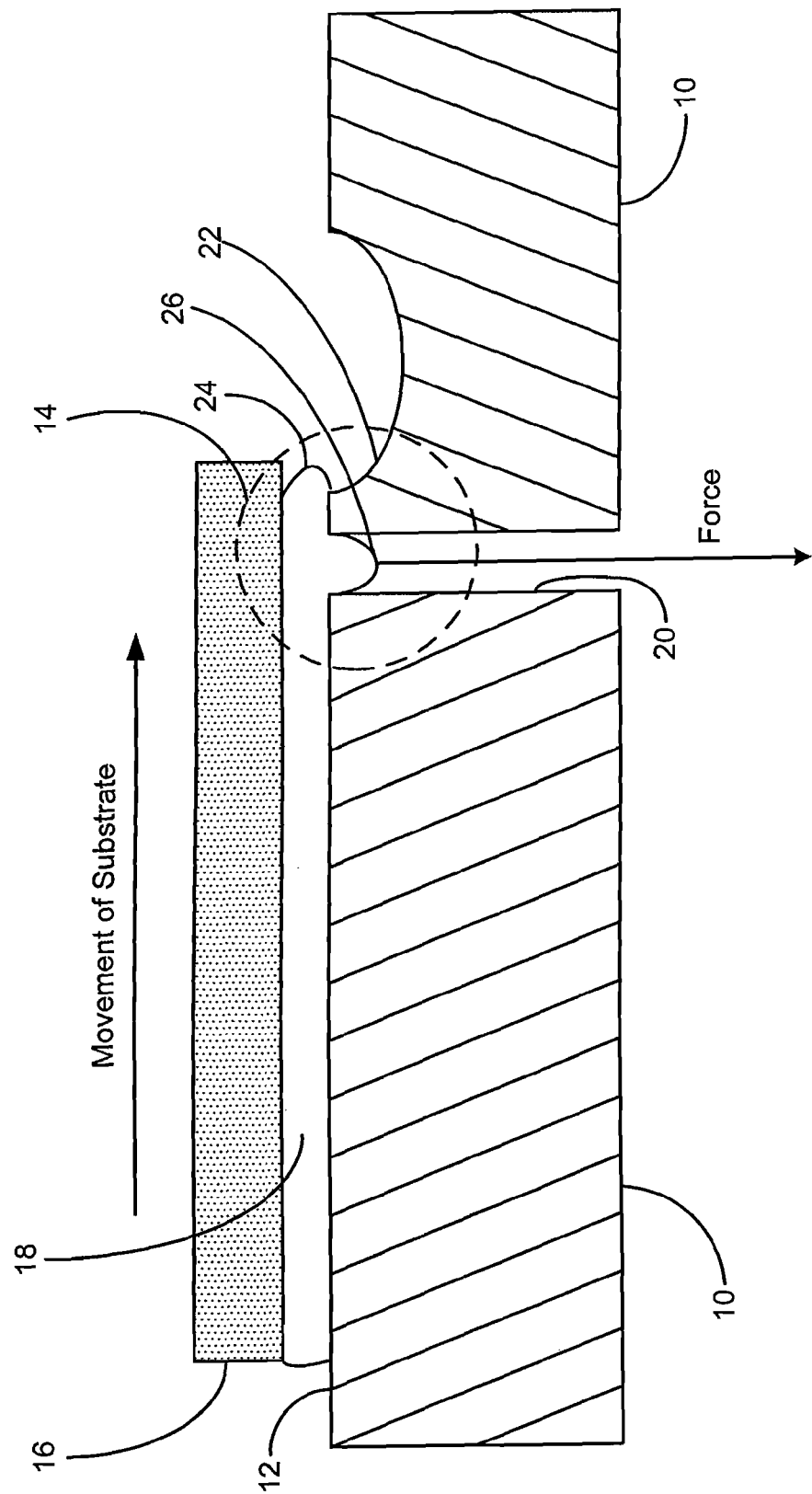
FIG. 1 is a schematic drawing showing an embodiment of a platen system incorporating a stripping element.

The following description of several embodiments describes non-limiting examples that further illustrate the invention. All titles of sections contained herein, including those appearing above, are not to be construed as limitations on the invention, but rather they are provided to structure the illustrative description of the invention that is provided by the specification.

Unless defined otherwise, all technical and scientific terms used herein have the same meanings as commonly understood by one skilled in the art to which the disclosed invention pertains. The singular forms "a," "an," and "the" include plural referents unless the context clearly indicates otherwise. Thus, for example, reference to "a stripping element" refers to one or more stripping elements, such as 2 or more stripping elements, 3 or more stripping elements, or even 4 or more stripping elements. Likewise, reference to "a platen" refers to one or more platens such as two or more platens, 3 or more platens or even 4 or more platens.

A "substantially flat substrate" refers to any object having at least one substantially flat surface, but more typically to any object having two substantially flat surfaces on opposite sides of the object, and even more typically to any object having opposed substantially flat surfaces, which opposed surfaces are equal in size but larger than any other surfaces on the object. A substantially flat substrate can be formed of any material, including a glass, silicon, a semiconductor material or a metal. Particular examples of substantially flat substrates include microscope slides (both 1"×3" slides and 25 mm×75 mm slides), SELDI and MALDI chips, and silicon wafers.

A "biological sample" refers to any sample obtained from, derived from or containing any organism including a plant, an animal, a microbe or even a virus. Particular examples of biological samples include tissue sections, cytology samples, sweat, tears, urine, feces, semen, pre-ejaculate, nipple aspirates, pus, sputum, blood, serum, tissue arrays, and protein and nucleic acid arrays.

A "liquid" refers to any substance in a fluid state having no fixed shape but a substantially fixed volume. Examples of liquids include solvents and solutions. A liquid can be polar or non-polar, organic or inorganic, volatile or non-volatile, high viscosity or low viscosity, an emulsion or a true solution. Examples of solvents include water, alcohols, polyols, hydrocarbons and ionic liquids. Examples of solutions include aqueous solutions of a dye, a protein (such as an antibody), a nucleic acid (such as a hybridization probe), a buffer, an acid, a base or a salt. Other examples of solutions include mixtures of two or more solvents.

In one aspect, a platen is disclosed for applying a liquid to a substantially flat substrate. The platen includes a liquid application station and a stripping element at an end of the liquid application station. A capillary space is defined between a substantially flat surface of the substrate and a substantially flat surface of the liquid application station. The capillary space can be maintained by a liquid present between the surfaces, but more typically the capillary space is maintained regardless of the presence or absence of a liquid in the capillary space by spacers (such as rails or protuberances) on the platen that serve to separate the surfaces. The separation between the surfaces that is defined by the spacers can be constant across the surface of the liquid application station or can vary across the liquid application station such that one portion of the capillary space between the surfaces can be narrower and have greater capillarity than a different portion of the capillary space between the surfaces. If the substrate and the liquid application station are moved relative to one another (the substrate, the liquid application station, or both, can move), the separation between the surfaces at any given location on the surface of the substrate can vary over time.

A stripping element located at an end of a liquid application station can be used to remove a liquid from the capillary space between the surfaces of the station and the substrate. FIG. 1 shows a schematic diagram of an embodiment of a platen 10 having a liquid application station 12 with a stripping element 14 located at an end of the station. Substantially flat substrate 16 is separated from a substantially flat surface of the liquid application station 12 by capillary space 18 (which is shown occupied by a liquid). Stripping element 14 includes intersecting gap 20 and air barrier 22. In particular embodiments, the intersecting gap and the air barrier are separated by less than about 0.080 inches, for example, less than about 0.040 inches such as less than about 0.010 inches. In other particular embodiments, the small surface separating the intersecting gap and the air barrier is coplanar with the liquid application surface. In yet other embodiments, the intersecting gap and the air barrier are separated by between about 0.005 inches and about 0.080 inches, for example, between about 0.020 inches and about 0.060 inches.

Again, with reference to FIG. 1, a liquid confined to capillary space 18 will tend to remain in the capillary space until the capillary space is diminished. In fact, a liquid will tend to remain confined between a substrate and a liquid application station even as a substrate is moved across a liquid application station, especially if the liquid application station is coated with a substance that has a lower surface energy with respect to the liquid than a surface of the substrate. However, as substrate 16 is moved over stripping element 14, air barrier 22 alters capillary space 18 at leading edge 24. In some embodiments, the air barrier is at least of a depth such that the distance between the substrate and the bottom of the air barrier is greater than the width of capillary space 18 and greater than the width of the intersecting gap 20, and thus air barrier has the lowest capillarity by comparison to the capillary space and the intersecting gap. In other embodiments, the air barrier has a depth that substantially breaks capillarity and terminates capillary space 18. As shown in FIG. 1, liquid retreating from leading edge 24 is drawn into intersecting gap 20 to form a secondary leading edge 26 by a force acting to pull the liquid away from the surface of the substrate (the force can act in any direction having a component perpendicular to the liquid-exposed surface of the substrate). Removal of the liquid is accomplished substantially through the intersecting gap. The microfluidic forces harnessed by disclosed stripping element 14 hinder droplet formation at leading edge 24 and thereby reduce the amount of residual liquid remaining on a substrate.

The force acting through an intersecting gap can be any combination of gravity, a capillary force, and a reduced pressure (vacuum) formed in the gap. More typically, however, the force will include at least a capillary force (the strength of which can depend on any combination of the dimension of the gap, the surface energy of the material forming the gap, and the presence of a wicking material, such as a fibrous material, in the gap). An intersecting gap can be of a width that is greater than, equal to, or less than the thickness of a capillary space at the point where the capillary space and intersecting gap meet. The intersecting gap typically extends through the platen to the side opposite the liquid application station, however, it also is possible for the intersecting gap to extend partially through the thickness of the platen and be configured such that it opens to one or both sides of the platen to permit liquids entrained in the intersecting gap to be removed such that additional liquid can be drawn into the gap.

The intersecting gap can extend across the entire platen, or it can extend across only a portion of the platen. It can take the shape of an elongate, parallel-sided gap, or it can have a circular or oval shape. In some embodiments, the gap can be a plurality of gaps, for example, a series of circular holes extending into and possibly through the platen.

Figure 2:
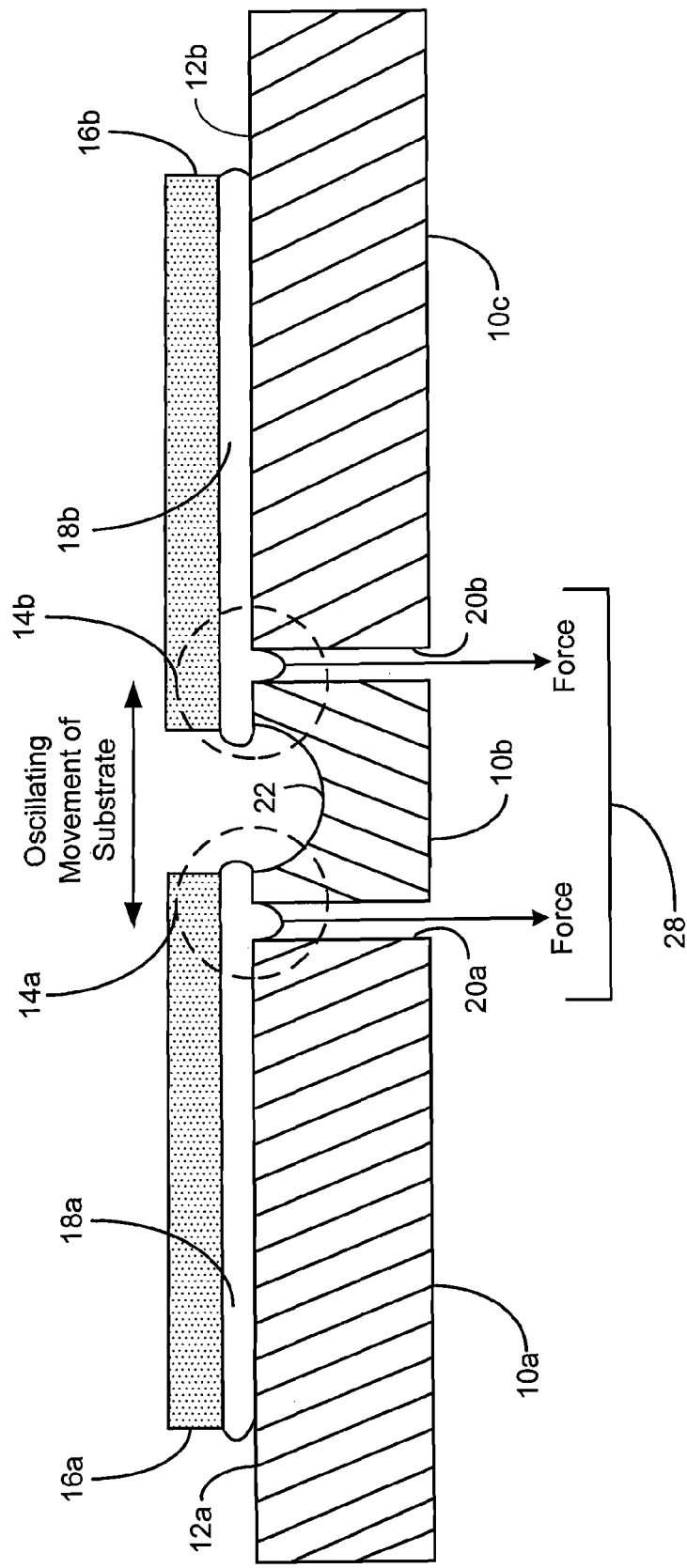
FIG. 2 is a schematic drawing showing an embodiment of a platen system incorporating a bi-directional stripping element.

FIG. 2 is a schematic diagram of a platen system incorporating a bi-directional stripping element 28. In this embodiment, the platen includes three portions, a first portion 10a including first liquid application station 12a, a second, central portion 10b including air barrier 22, and a third portion 10c including a second liquid application station 12b. On either side of the central portion 10b are first and second intersecting gaps 20a and 20b. Together, first intersecting gap 20a and air barrier 22 form a first stripping element 14a, and together, second intersecting gap 20b and air barrier 22 form a second stripping element 14b. Stripping elements 14a and 14b, which share air barrier 22, together form bi-directional stripping element 28. Although the bi-directional element shown in FIG. 2 includes a single, shared air barrier, other embodiments of a bi-directional stripping element can have multiple (such as 2 or more) air barriers between at least two intersecting gaps. Intersecting gaps 20a and 20b can be independently connected to different waste containers to permit waste liquid segregation, or can be connected to a single waste container.

In operation, as shown in FIG. 2, a platen system incorporating a bi-directional stripping element can be used to successively apply and remove liquids (which can be the same or different) by moving the substrate back and forth between the two liquid application stations 12a and 12b. A first liquid applied to a substrate while the substrate is located at a first liquid application station is substantially removed through the associated intersecting gap (such as 20a) of that half of the bi-directional stripping element as the substrate is moved to the second liquid application station for application of a second liquid (which again can be the same or different as the first liquid). As the substrate is moved back from the second liquid application station toward the first, the liquid applied on the second station is substantially removed through the intersecting gap (such as 20b) associated with the other half of the bi-directional stripping element. The oscillating process can be repeated as many times as desired to treat a substrate with multiple liquids (such as multiple reagent solutions) and/or treat the substrate multiple times with the same liquid (such as a rinse solution or a solvent).

Figure 3:
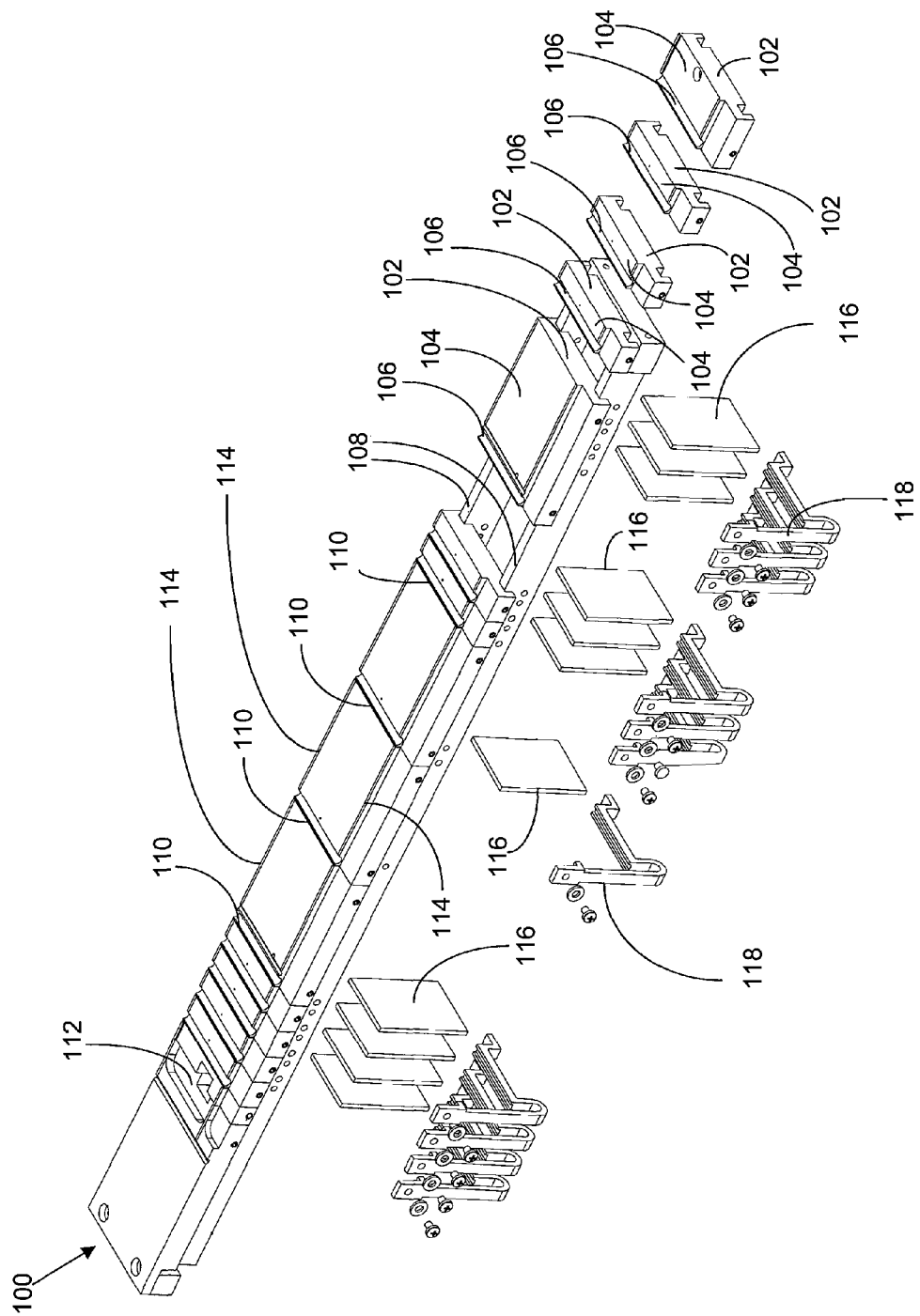
FIG. 3 is an isometric drawing of a configurable platen system incorporating a plurality of platen segments.

FIG. 3 is a perspective diagram showing an embodiment of a platen 100 including a plurality of platen segments 102. In this embodiment, the platen segments 102 include a liquid application station section 104 and an air barrier section 106. When the platen segments 102 are held together on support rails 108, a plurality of intersecting gaps 110 are formed at the interfaces between pairs of platen segments. An air barrier 106 of one platen segment and an intersecting gap 110 formed with an adjacent platen segment together form a stripping element as illustrated in FIG. 1. A substrate positioning segment 112 is located at one end of the platen to orient a substrate onto the platen at a first end, and a substrate can then be conveyed across the platen segments by a substrate transporter. The substrate positioning segment also can include a slide detector and/or a code reader for reading a code on a substrate. A substrate is supported on spacer rails 114 located on the lateral edges of the liquid application stations 104 of the platen segments, which spacer rails function to maintain a capillary space between the substantially flat surface of a substrate and the substantially flat surface of the liquid application stations. Also illustrated in FIG. 3 are absorbent pads 116 that can be included to capture liquids that pass through intersecting gaps 110 to the lower side of the platen 100. In this embodiment, the absorbent pads are supported by L-brackets 118 that can be removably fastened to the platen such that the absorbent pads can be conveniently replaced once they are saturated with waste liquids. Separate absorbent pads serve to segregate waste liquids from different liquid application stations and simplify waste handling, both by preventing co-mingling of wastes and by transforming liquid wastes into a "solid" form. The absorbent pads illustrated in the embodiment of FIG. 3 are only one embodiment where wastes from the intersecting gaps of different stripping elements can be collected and segregated. For example, the wastes from different stripping elements can simply be directed to different containers, and some wastes (such as a solvent applied at multiple stations) can be directed to the same container while other wastes are directed to one or more containers, together or separately. In addition to the waste segregation function, contact of an absorbent pad to or insertion of the same into an intersecting gap of a stripping element also can provide a capillary force that helps to draw a liquid into the intersecting gap, which force can be in addition to a capillary force exerted by the intersecting gap itself. In another embodiment, a single, disposable absorbent waste pad can be put in contact with the intersecting gaps along the length of the platen. In a more particular embodiment, the single, disposable absorbent pad is segmented (for example with liquid barriers) such that wastes from different portions of the platen are segregated along the length of the pad.

A disclosed stripping element can remove substantially all of the liquid applied to a substrate on a liquid application station. For example, in some embodiments, less than about 20 microliters of residual liquid is left on a substrate surface after being passed over the stripping element (for example, less than about 15 microliters, less than about 10 microliters or even less than about 5 microliters of residual liquid is left on the substrate surface). In one embodiment, a 100 microliter application of a liquid to a standard glass 1" by 3" microscope slide leaves a residual volume on the slide of between about 0.5 microliters and about 3 microliters after passing the slide across a stripping element. The highly efficient way in which liquids are removed by a stripping element minimizes the number of rinses necessary to dramatically reduce the amount of reagent carryover between liquid application stations. For example, reagent carryover from one liquid application station used to apply a reagent to another station used to apply a reagent can be reduced by a factor of approximately $10^6$ by a single intervening rinse station incorporating a stripping element [for example, a 100 microliter reagent application is reduced to 1 microliter at a first stripping element (a factor of $10^2$), diluted with 100 microliters at a rinse station (another factor of $10^2$), and then stripped again to 1 microliter (yet another factor of $10^2$)].

Although not shown in FIGS. 1-3, a liquid application station of a platen also can include a heater and/or cooler (such as a resistive heater, radiant heater, microwave heater, ultrasonic heater or a Peltier device) that can be used to raise or lower the temperature of a liquid (and a sample and a substrate as well). Where a platen includes a plurality of liquid applications stations, two or more of these liquid application stations can include heaters (and/or coolers) that are independently controlled (to achieve the same or different temperatures/heating or cooling rates) or controlled together (to achieve substantially the same temperature/heating or cooling rate). It is also possible to have the heaters for several stations controlled together and heaters of one or more other stations controlled independently. Insulating segments or sections can be added between platen stations (such as between different platen segments) to provide thermal isolation.

Another possible modification of a platen according to the disclosure is treatment of the platen surface with a substance that reduces adhesion of a liquid or a component of a solution (such as a protein) to the platen surface. In a particular embodiment, a non-polar substance is applied to the platen surface to reduce adhesion of a polar liquid. For example, a wax or a fluorinated hydrocarbon (e.g. Teflon®) coating can be applied to the platen surface to reduce adhesion of an aqueous liquid. Surface treatments further minimize residual liquid adhered to a liquid application surface, thereby minimizing carryover contamination.

As shown in FIG. 3, the platen can include multiple coplanar liquid application stations that can be used in combination to successively apply a series of reagents (such as solvents and solutions containing specific dye molecules or labeled specific binding moieties) to a substrate conveyed across the platen. The liquid application stations can be of a width (in the direction the substrates are moved) that is less than, equal to, or greater in width than the substrate (in the direction that it is moved). If the stations are of a width that is smaller than the width of the substrate, multiple liquids can be applied and/or removed to a substrate at the same time. In FIG. 3, the platen is modular and hence configurable because the individual platen segments can be assembled in any order, and as will be discussed later, such differing orders can be utilized to accomplish different staining protocols. However in other embodiments a platen can be monolithic (constructed from a single piece of material) or can be partially monolithic and partially modular. Modularity lowers manufacturing costs and improves field serviceability.

Figure 15:
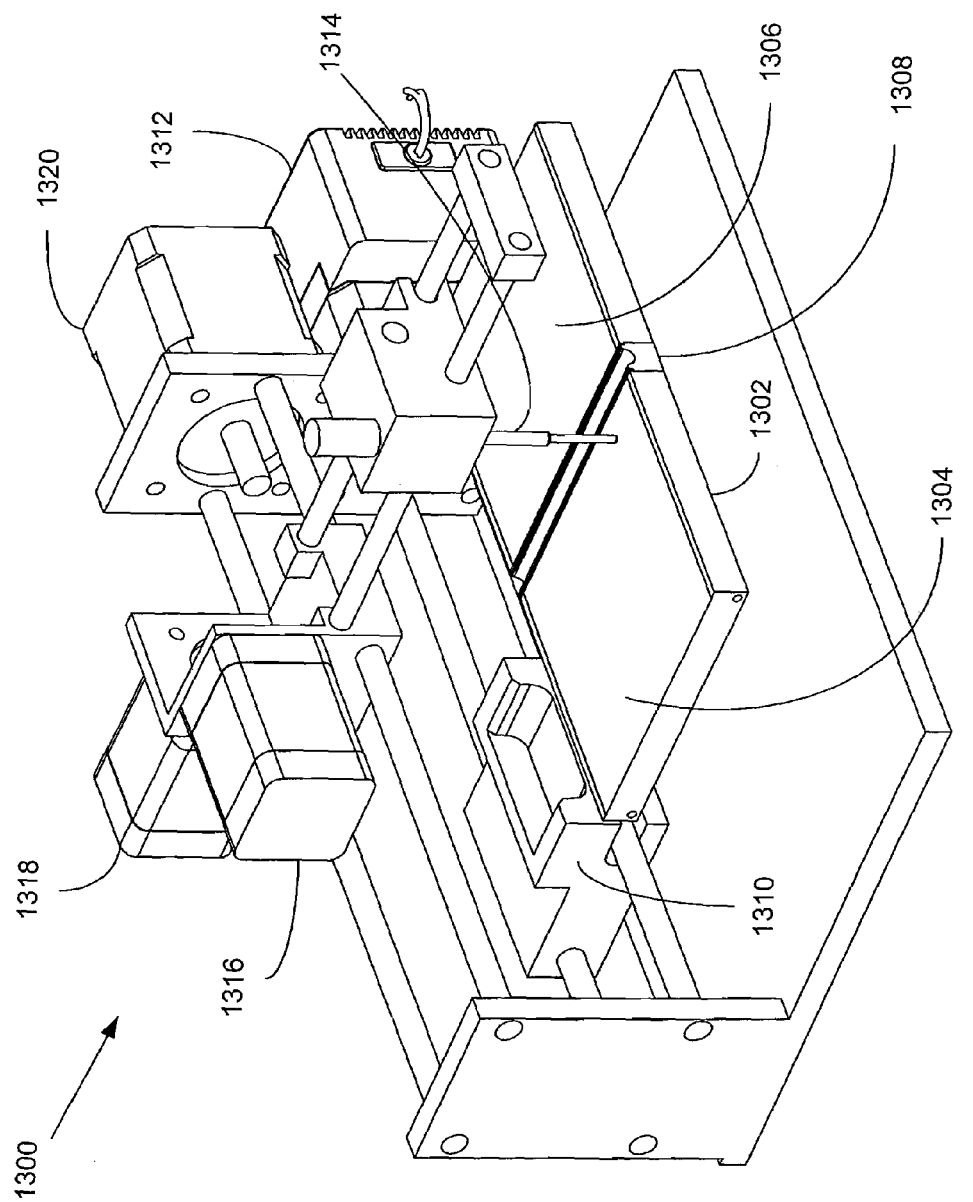
FIG. 15 is a perspective drawing of an embodiment of substrate treatment module incorporating a bi-directional stripping element.

In another aspect, an apparatus is disclosed for contacting a liquid to a surface of a substantially flat substrate. In one embodiment, the apparatus includes a substrate transporter, a liquid applicator and a platen. The platen includes a liquid application station and a stripping element at an end of the station, wherein the stripping element includes an intersecting gap and an air barrier. The substrate transporter functions to convey a substrate (such as a microscope slide bearing a biological sample) along the platen. Any means to convey the substrate along a platen can function as the substrate transporter, but in particular embodiments, the substrate transporter can be one or more of a belt drive, a screw drive, a chain drive, and a slide drive. A screw drive suitable for use in the disclosed apparatus is described in U.S. Pat. No. 3,431,886 and a chain drive suitable for use in the disclosed apparatus is described in U.S. Pat. No. 4,088,797. Belts having tabs to engage and move a substrate along a platen can replace the tabbed chains of the chain drive as described in U.S. Pat. No. 4,088,797. A slide drive is illustrated in FIG. 15.

The liquid applicator serves to deliver a liquid to a liquid application station of the platen where the liquid is contacted to a surface of the substrate, and in particular, to a surface of a substrate bearing a biological sample.

Figure 4A:
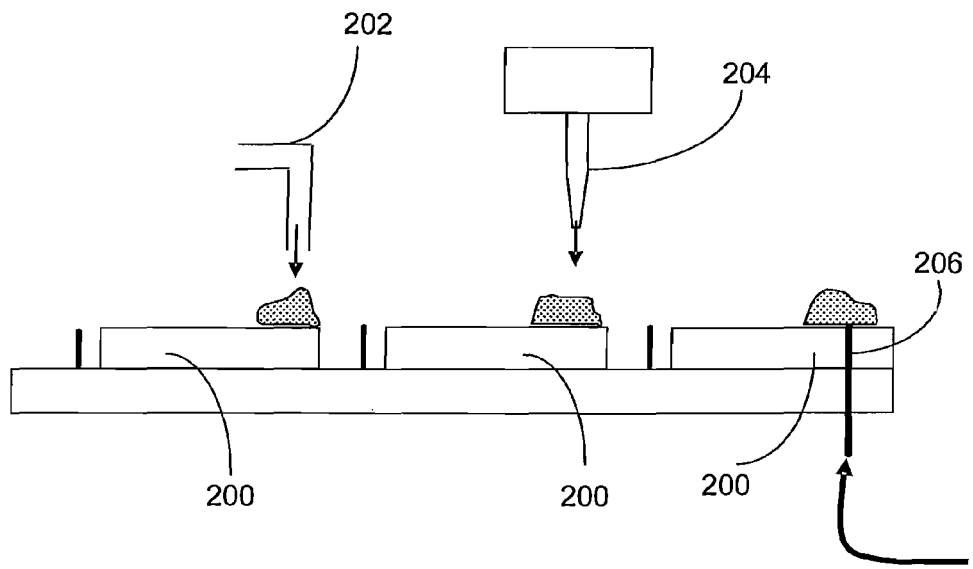
FIG. 4A is a schematic diagram illustrating several embodiments of a liquid applicator for delivery of a liquid to a liquid application station of a platen.
Figure 4B:
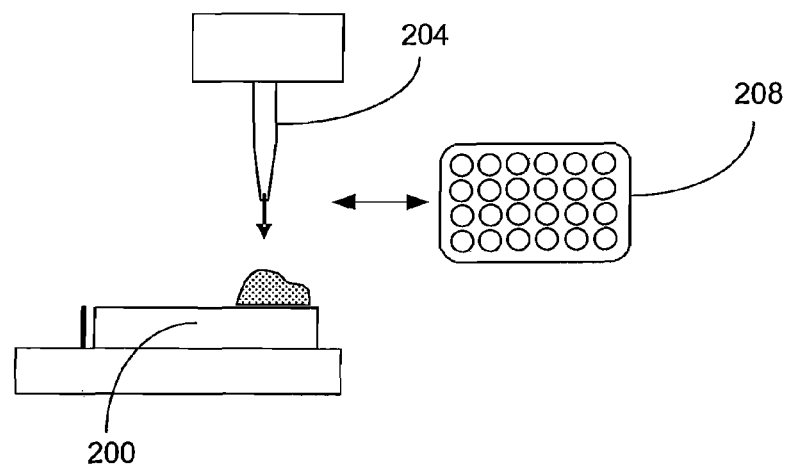
FIG. 4B is a schematic diagram illustrating a combination of a robotic dispenser and a multi-well plate for selective delivery of a variety of different reagents to one or more liquid application stations of a platen.

The liquid applicator of the apparatus can be any means that delivers a liquid to a liquid application station of a platen, either directly or indirectly. In a particular embodiment, a liquid applicator delivers a liquid to a capillary space formed between a substantially flat surface of a substrate and a substantially flat surface of a liquid application station. In particular examples, as shown in the schematic diagrams of FIG. 4A, the liquid applicator of the disclosed apparatus that delivers a liquid to a liquid application station 200 can be one or more of a stationary (or moveable) nozzle 202, a robotic dispenser under microprocessor control 204, and an aperture through the platen 206. In a more particular example, as shown in FIG. 4B, a plurality of different liquids can be delivered to a liquid application station 200 using a robotic dispenser 204 in combination with a multi-well plate 208. The plate can hold a plurality of liquids, that can be selectively retrieved by the dispenser under computer control and then delivered to a particular liquid application station of a platen. A robotic dispenser in combination with the multi-well plate (such as a 12-, 24-, 48-, or 96-well plate) allows greater flexibility in the substrate treatment regimens that can be performed by the apparatus.

In addition to the advantages associated with removing liquids from a substrate surface using the microfluidic forces at work in the disclosed stripping element, in some embodiments, microfluidic forces also are utilized to improve application of liquids to a substrate. FIG. 5 is a set of schematic series diagrams illustrating microfluidic featuring of a liquid application station. Also illustrated is an improved robotic liquid application method.

Figure 5A:
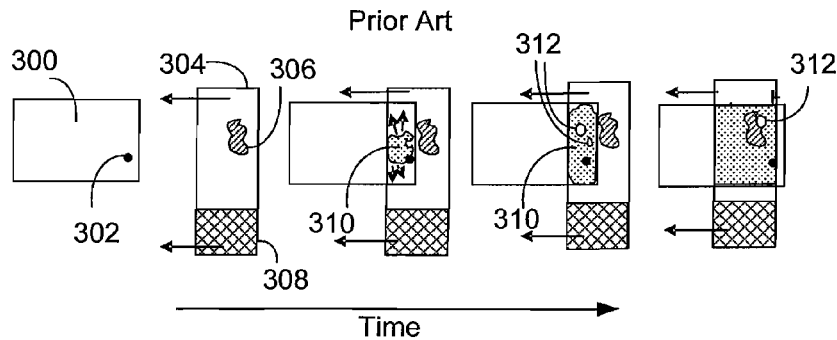
FIGS. 5A-D are schematic diagrams showing time-series that illustrate how microfluidic featuring of a liquid application station can improve substrate treatment.

In all of FIGS. 5A-5D, a microscope slide 304 (optionally labeled with a machine readable code 308) bearing a biological sample 306 (such as a tissue section) is shown moving across a liquid application station 300 (sample side facing the liquid application station) in each series of diagrams from left to right. FIG. 5A illustrates a problem that can arise when an aperture 302 in the substantially flat liquid application station 300 is utilized to apply a liquid to a substrate bearing a biological sample. Once slide 304 is positioned over the aperture, liquid 310 is dispensed into a capillary space between the surface of the liquid application station and the surface of the slide to which the sample is adhered (second diagram in the series of FIG. 5A). As liquid migrates radially outward from aperture 302 into the capillary space, air bubbles 312 tend to form as shown in the third diagram of the series of FIG. 5A. During the spreading process, focal surface quality variances of the substrate can lead to loss of inter-phase control resulting in such air bubble inclusions. Alternatively, air trapped within the liquid dispense line may be introduced into the capillary space. As shown in the fourth diagram of the series, an air bubble 312 formed in the spreading liquid can associate with the biological sample 306. An air bubble that becomes associated with a sample can prevent a reagent from contacting the sample, leading to inconsistent treatment across the sample such as incomplete staining of a sample.

Figure 5B:
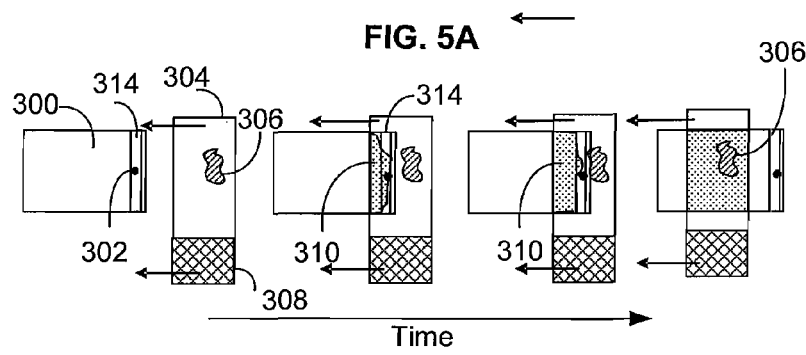
Figure 5C:
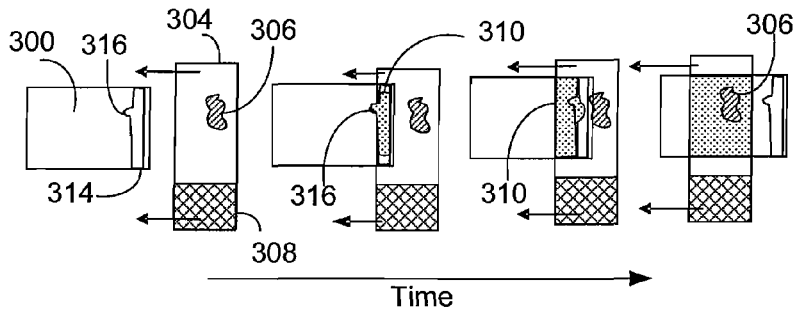

FIGS. 5B and 5C illustrate a liquid application station including a fluid phase trap that provides a number of advantages over the station shown in FIG. 5A. In the embodiment of FIG. 5B, liquid application station 300 also includes channel 314 in the liquid application station's otherwise substantially flat surface that acts as a potential reservoir for a liquid to be dispensed therein. An aperture 302 for liquid delivery is shown located at the bottom of channel 314, but it also is possible to include an aperture positioned on an end and/or side of the channel. In general, the channel can be of a length that extends across at least a portion of the width of the liquid application station and of a depth and width such that the channel can contain a desired amount of a liquid to be used in treating the substrate (for example, the channel can be dimensioned to contain up to 300 microliters, such as up to 200 microliters or up to 100 microliters), which will depend on the maximal volume of the capillary space defined between a substrate and a liquid application station. In general, the channel can be of sufficient capacity to contain the volume of liquid needed to completely fill the maximal capillary space, without being so large (or deep) as to prevent contact of the liquid with the capillary space as the substrate moves past the channel. In a particular embodiment, a channel is a hemispherical channel, and in a more particular embodiment, the channel is about 0.030" deep and about 0.090" wide in the direction the substrate is moved across the channel, and can extend transversely across at least a portion of a liquid application station. Cut channel edges can be sanded down (radiused), polished and treated with a liquid repelling coating (such as a wax or Teflon®) to reduce the tendency for a liquid to remain in the channel.

The second diagram in the schematic series of FIG. 5B illustrates how dispensing a liquid 316 into a channel 314 allows the liquid to spread laterally from aperture 302 into the capillary space between the liquid application station and the substrate. In one embodiment, as the substrate moves into position over the channel a capillary space is formed between the bottom of the channel and the substrate. The liquid dispensed into the channel then moves laterally from the aperture to fill this capillary space. Then, as the substrate moves further past channel 314, liquid 310 is pulled from the lower capillary force space over the channel and into the higher capillary force space between the substrate and the liquid application station (third in the series of FIG. 5B). Any foam and/or entrapped air bubbles tend to stay within the channel, and as the slide continues to translate, liquid continues to exit out of the channel into the growing capillary space between the substrate and the liquid application station. Since the thinner capillary space presents a stronger capillary force than the thicker space over the channel, the liquid is preferentially captivated and pulled forward. On the other hand, air pockets (foam) preferentially stay behind in the larger spaced channel. Spreading and captivation of the liquid in this manner helps to eliminate bubbles in the liquid such that when a biological sample 306 is contacted with the liquid (fourth in the diagrammatic series of FIG. 5B) no bubbles will become associated with the sample.

In one aspect, a channel serves as reservoir capacity for rapidly storing injected liquid in a focal organized fashion. The channel also makes it possible to deliver the liquid in a bolus, thereby obviating the need for a steady, slow, precise, and expensive pumping means for liquid delivery. The channel also directs and orients the injected liquid in an orderly manner, thereby overcoming the natural radial flow pattern. Furthermore, the channel serves to selectively retain air bubble inclusions while permitting orderly bubble-free liquid entry into the growing capillary space that is formed as a substrate is conveyed along the liquid application station. As liquid leaves the channel and moves into the capillary space, the partitioned gas pocket(s) are concentrated and break, resulting in the elimination of an inter-phase and promoting uniform coverage of a substrate surface. Assuming an excess of liquid (beyond the total capacity of the fully formed capillary space between the substrate and liquid application surfaces) is not introduced into the channel, substantially no residual liquid will remain in the channel once the substrate has moved completely over the channel. Appropriate channel edge radiuses, surface finish (smoothness), and surface energy (determined by the channel surface chemistry) can further improve the tendency of a liquid to flow smoothly and completely from a channel into a capillary space as a substrate is conveyed across the channel. In particular, a higher level of smoothness and a lower surface energy will favor migration of the liquid from the channel to the capillary space, whereas more surface imperfections and higher surface energy will tend to retain liquid in the channel, where it could contaminate a subsequently delivered liquid.

Also, while the channel's length generally is positioned substantially perpendicular to the direction in which the substrate is moved across the liquid application station (as shown in FIG. 5B), it is also possible to use a channel that forms an acute angle with a leading edge of the substrate. However, since a substrate is typically conveyed across a liquid application station such that the leading edge of the substrate forms an oblique angle with respect to the direction that the substrate is moved by the substrate transporter, the leading edge of the substrate will approach the channel at an acute angle even if the channel is perpendicular to the direction of motion of the substrate.

In the embodiment of FIG. 5C, liquid application station 300 includes a channel 314 and a divot 316 in a trailing edge of the channel (relative to the direction of motion of substrate 304). A liquid applicator such as a robotic dispenser or a fixed or movable nozzle can be used to deliver a liquid to the channel via the divot. The second diagram in the series of FIG. 5C shows how a liquid introduced into divot 316 when substrate 304 is otherwise covering channel 314 will spread laterally inside the channel and along the capillary space at the interface of the leading edge of the substrate and the trailing edge of the channel. In a particular embodiment, a liquid is dispensed to the divot using a robotic dispenser just before the divot is covered by the advancing substrate to enhance the spreading effect. By spreading the liquid laterally, the liquid will be pulled evenly into the capillary space as the substrate is conveyed further across the liquid application station (third in series of FIG. 5C), and the biological sample will be treated more evenly and there is a reduced likelihood of bubbles interfering with the treatment (fourth in the series of FIG. 5C). In a more particular embodiment, the divot is treated with a liquid-adhesive coating (such as a hydrophilic coating) to facilitate captivation of a dispensed liquid, which treatment can be differential to a treatment used on other portions of the platen (such as a liquid-repelling applied to a liquid application station).

In summary, the advantages of incorporating a fluid phase trap is that the injection rate is far less critical, liquid flow is far more oriented and controlled, reservoir capacity buffers against over-flow outside the domain of the capillary space, slide-to-slide liquid isolation can be achieved, surface liquid residual can be substantially eliminated, inter-phase air inclusions can be isolated and trapped, and sensitivity of surface coverage to focal substrate surface quality variances and/or entrained gas within liquid lines can be reduced. Total volume injection may still requires some level of precision so as to avoid over-filling that would lead to leaving excess liquid behind in the channel after translation.

Figure 5D:
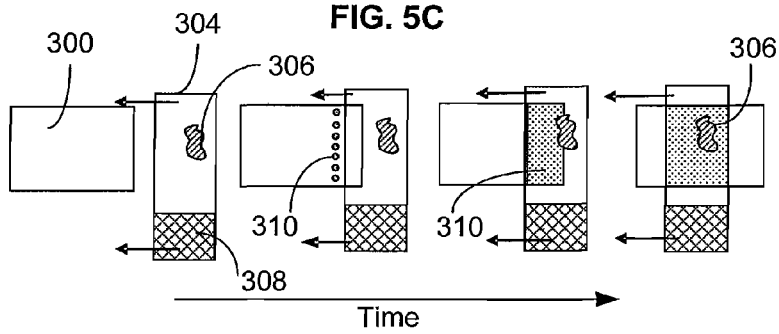

In the embodiment of FIG. 5D, no fluid trap is employed to deliver a liquid to the liquid application station. Rather, as shown in the second diagram in the series of FIG. 5D, a liquid 310 is delivered directly to the substantially flat surface of the liquid application station in one or more spots (such as two or more, three or more, four or more, or even five or more spots) at any point across the path that the substrate will follow over the station (typically near the leading edge of a liquid application station just prior to movement of the substrate onto the liquid application station). The liquid spots can be deposited using a moveable nozzle, a manifold of nozzles or a robotic dispenser. By spreading the liquid across the path of the advancing substrate in a series of spots, the liquid will spread more evenly into the capillary space between the substrate and the liquid application station (third diagram in the series of FIG. 5D). The even spread helps to prevent bubble formation and thereby provides more even contact of the liquid to the biological sample 306, as shown in the fourth diagram in the series of FIG. 5D.

FIG. 6 is a series of schematic diagrams illustrating additional modifications that can be made to a platen surface and/or to the method of delivering a liquid to the platen surface that permit even greater process flexibility. In FIG. 6A, a liquid application station 400 includes a fluid phase trap 402 (such as the channel shown) including a plurality of apertures 404 that are used to deliver one or more liquids to the depression. The liquids delivered to the channel through the plurality of apertures can be the same or different, and it is also possible to deliver several liquids through the apertures at the same or different times. In one embodiment, two liquids that need to be mixed are added the depression at the same time and allowed to mix (or be actively mixed such as by vibration) prior to substrate 408 being moved past the depression. In another embodiment, a first aperture delivers a reagent and a second delivers a rinse agent that can be used for routine maintenance of the liquid application station surface.

Figure 6A:
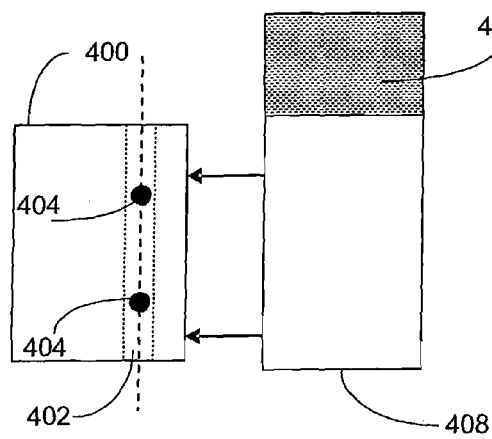
FIGS. 6A-D are schematic diagrams showing additional alternative modes and configurations for applying one or more liquids to a liquid application station of a platen.
Figure 6B:
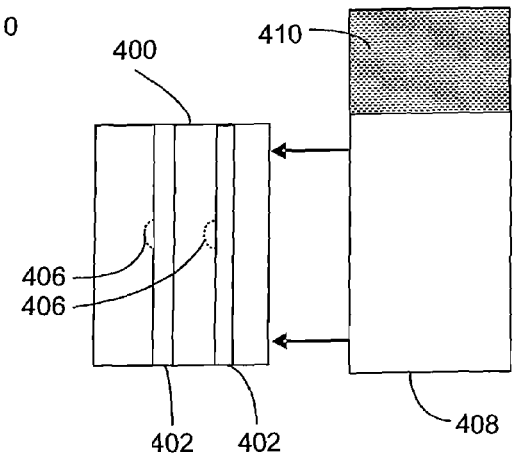
Figure 6C:
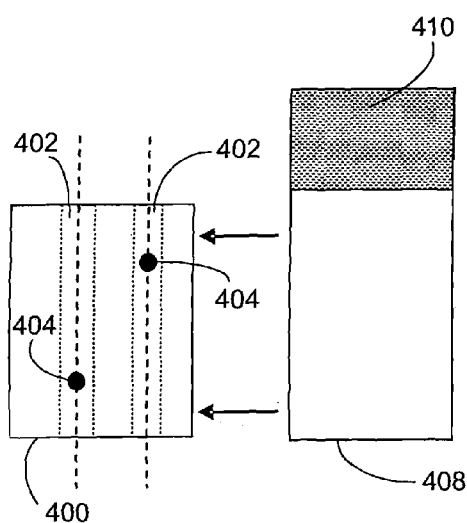
Figure 6D:
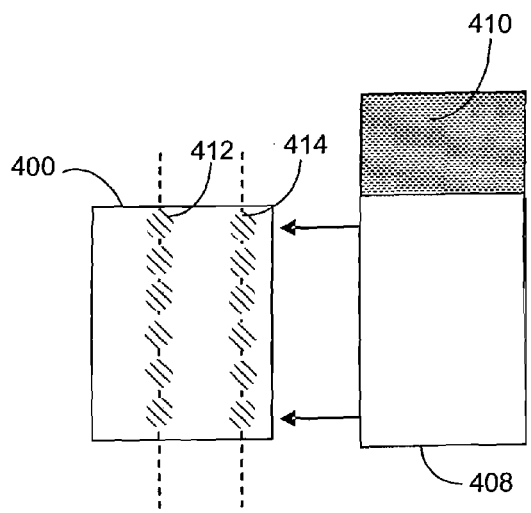

The substrate 408 in the embodiment of FIG. 6A (and the embodiments of FIGS. 6B, 6C and 6D) includes a machine-readable code 410 (such as a one- or multi-dimensional barcode or infoglyph, an RFID tag, a Bragg-diffraction grating, a magnetic stripe or a nanobarcode) with coded instructions that specify the type, sequence, and timing of the liquid(s) delivered to a liquid application station for treatment of a particular substrate. In FIG. 6B, a liquid application station 400 includes a plurality of channels 402 having divots 406 at their trailing edges. In this embodiment, the channels are spaced along the liquid application station surface to permit sequential application of one or more liquids (that can be the same or different) to a substrate as the substrate is moved across the station. In FIG. 6C, another multi-channel embodiment is shown. In this case, however, liquid application station 400 includes a plurality of channels 402 each having an aperture 404 for liquid delivery to the channels. In FIG. 6D, a method is illustrated of applying one or more liquids to a liquid application station 400, where a first liquid is dispensed in a plurality of spots at one location 412 across the substrate's path and a second liquid (which could be the same or different) is dispensed in a second plurality of spots at a second location 414 across the substrate's path.

Any number of liquid dispensers can be positioned along the length of a liquid application station. Alternatively, or one or more moveable dispensers such as one or more robotic dispensers can be used to dispense one or more liquids at any point or points along the length of a liquid application station. Not only do such configurations provide process flexibility with regard to the types and combinations of liquids that are applied to a substrate on a particular liquid application station, they also provide additional process flexibility with regard to the incubation time of a substrate on a particular liquid application station. For a liquid application station of fixed length, it is possible to vary the time a substrate spends exposed to a liquid (incubation time) by varying the rate at which the substrate is moved along the station. Altering the point on the station where the liquid is applied also can serve to alter the incubation time. For example, if a liquid is applied to the substrate once it has already traversed ½ of the length of a station, the incubation time is cut in half. In a multi-station platen system, the difference between altering the rate of movement of substrates along the platen and altering the liquid delivery point on a given liquid application station is significant. Whereas when the rate is changed the incubation time on all stations along the platen is changed, when the delivery point is changed on a particular liquid application, only the incubation time on that particular station is changed. For complex staining protocols such as ISH and IHC protocols, the ability to independently control the incubation time for a particular, time-sensitive step (such as a hybridization step) is particularly important. Another important advantage to altering the delivery point is that it does not alter the overall flow of multiple substrates across a platen, which permits pacing to other laboratory process that can improve laboratory workflow.

Figure 7:
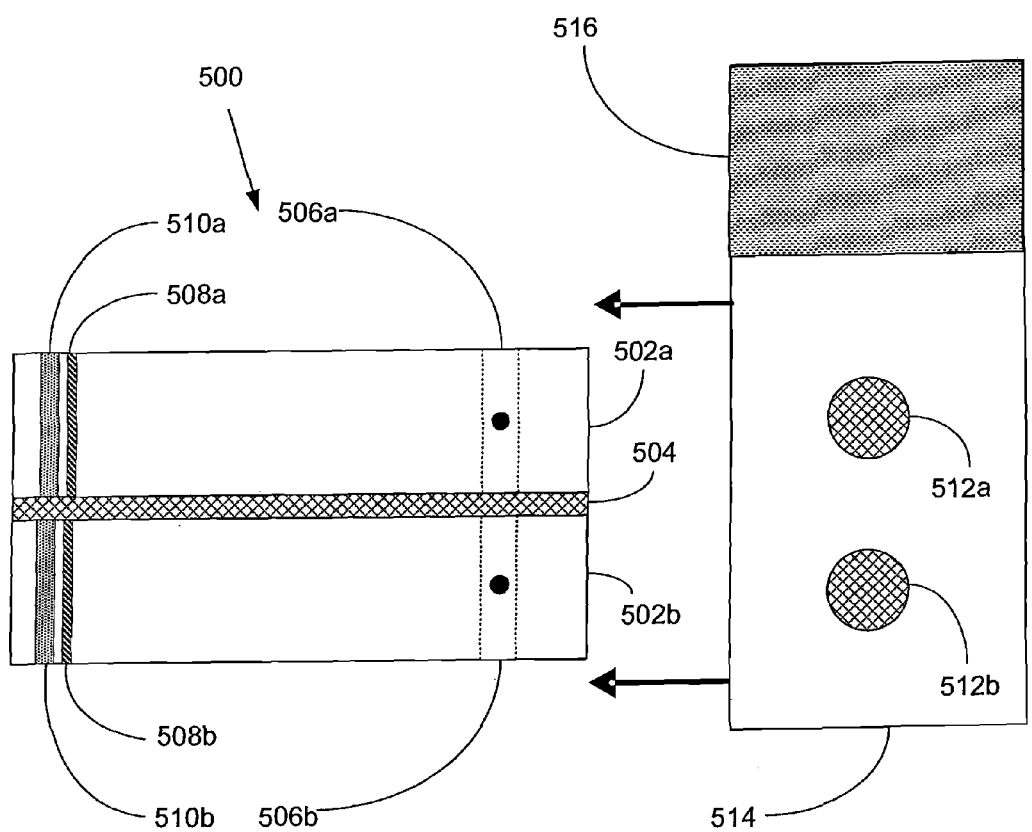
FIG. 7 is a schematic drawing showing an embodiment of a segmented liquid application station.

It also is possible to segment a liquid application station such that different portions of a substrate are treated separately with the same or different liquids. A simple embodiment of this aspect is shown in FIG. 7. In this embodiment, liquid application station 500 includes a first station segment 502a and a second station segment 502b that are separated by liquid barrier 504 (which can, for example, be an air gap or a liquid-repellent-treated strip). Although two such station segments are illustrated, it is possible to have 3 or more, 4 or more, 5 or more, or even 6 or more such segments, which segments can be of different lengths, aligned or staggered in configuration (see U.S. Pat. No. 4,200,056).

In the embodiment of FIG. 7, station segments 502a and 502b include liquid applicators, 506a and 506b, respectively. In this case, the liquid applicator for each station segment is an aperture that delivers a liquid to a channel acting as a fluid phase trap. A stripping element on segment 502a includes intersecting gap 508a and air barrier 510a, and a stripping element on segment 502b includes intersecting gap 508b and air barrier 510b. Samples such as first and second biological samples 512a and 512b can be mounted on the underside of substrate 514 which substrate is moved across the parallel station segments in the indicated direction. Because the station segments are fluidically isolated by liquid barrier 504, the first and second samples can be treated with the same or different liquids on the same liquid application station. In this embodiment, substrate 514 also includes machine readable code 516, which can include coded instructions that specify the liquid(s) delivered to the station as well as sample/patient/physician/laboratory information for each of the samples borne by the substrate. Examples of machine-readable codes that can be used include linear barcodes (such as code 128), multi-dimensional barcodes (such as optical characters, data matrices and infoglyphs), RFID tags, Bragg-diffraction gratings, magnetic stripes, or nanobarcodes (such as spatial and spectral patterns of fluorescent nanoparticles or spatial patterns of magnetic nanoparticles).

Figure 8:
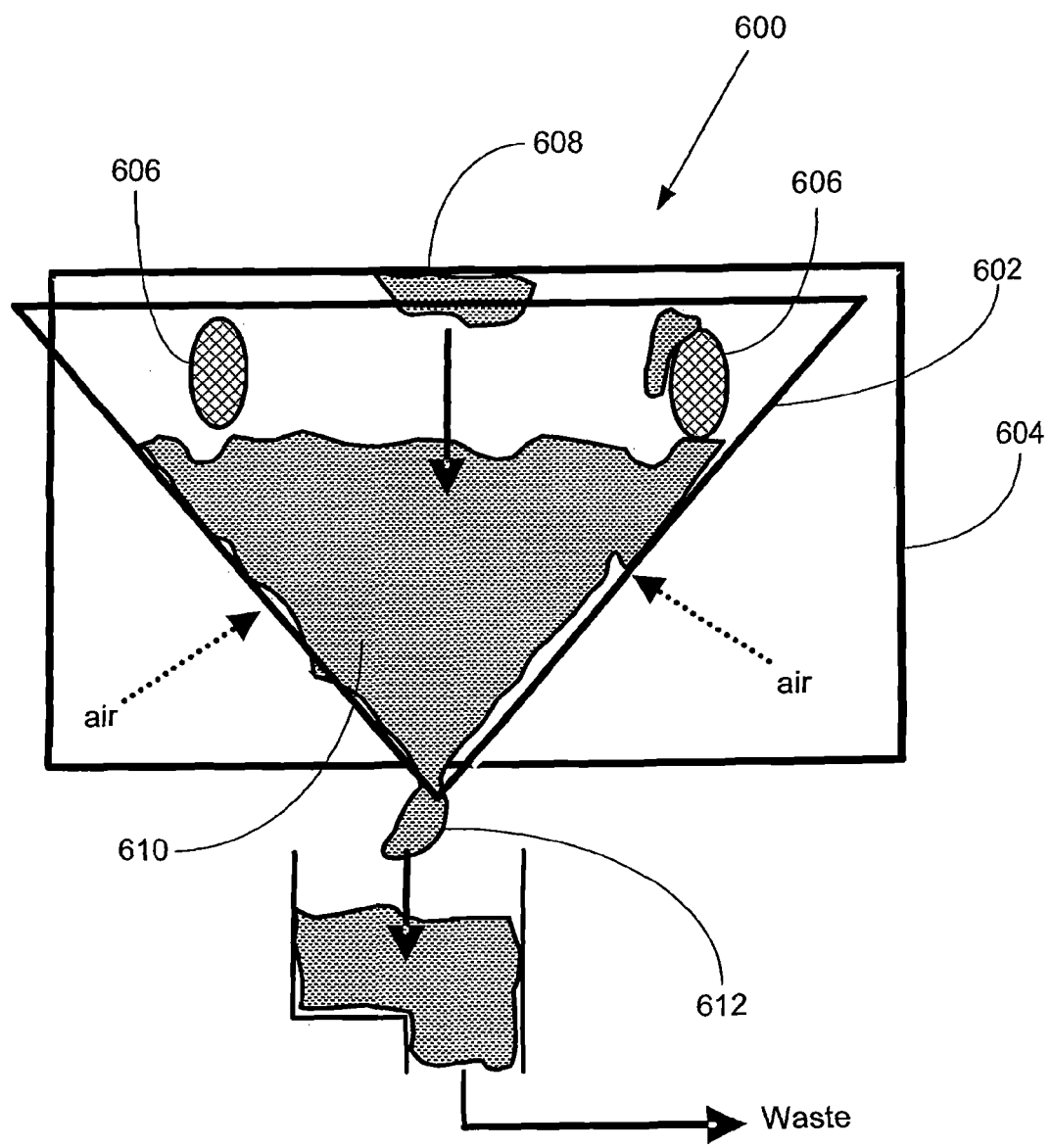
FIG. 8 is a schematic diagram illustrating an embodiment of an intersecting gap of a stripping element.

FIG. 8 is a schematic diagram illustrating an embodiment of an intersecting gap 600 of a stripping element. In this embodiment, the intersecting gap includes additional microfluidic features that help improve clearance of liquids from the gap after they are removed from a substrate passed over a stripping element. Intersecting gap 600 includes triangular liquid-directing plate 602 and backing plate 604 (which can be part of a platen segment), which plates are held in capillary separation by posts 606. As a substrate moves across the intersecting gap, liquid 608 that has been removed from the substrate is drawn down into the intersecting gap by capillary forces. As the liquid builds up in mass, gravity eventually exerts sufficient force to compel the drops into a falling film down through the gap and eventually into a larger liquid reservoir 610 that is held in positional stasis by capillarity. Capillarity maintains liquid captivation along the triangular sides and the liquid is routed toward the bottom point of the triangular plate where gravity exerts its greatest force. To further assist removal of the liquid from the reservoir as drop 612, effective venting can be provided such that air can replace the void left by the liquid vacating the reservoir. In this instance, there are no enchambering sides to the intersecting capillary gap, providing ample venting that promotes free fall of liquid throughout the gap. If capillarity were too strong inside the gap and/or venting was not provided, it is possible that the entire gap could fill with liquid, thereby blocking entrance of additional liquid into the top of the intersecting gap.

An important feature of the intersecting gap shown in FIG. 8 is that the processes by which liquids are moved away from the substrate, into and through the intersecting gap, and finally to waste, are all thermodynamically (passively) driven. No active mechanized pumping or routing means are required making the design simple and reliable. In other embodiments, capillary forces can further be utilized to promote conduction of liquid through the intersecting gap by providing an intersecting gap wherein the gap's width decreases with distance away from the entrance of the intersecting gap. In such an embodiment, the smaller width, having higher capillarity, will tend to attract the liquid away from the wider portion near the entrance that exhibits less capillarity. Contact of the intersecting gap with a wicking material (such as at a distal opening used to remove liquids from the gap) and application of a vacuum to the gap also can further improve conduction of a liquid through and out of the intersecting gap.

Figure 9:
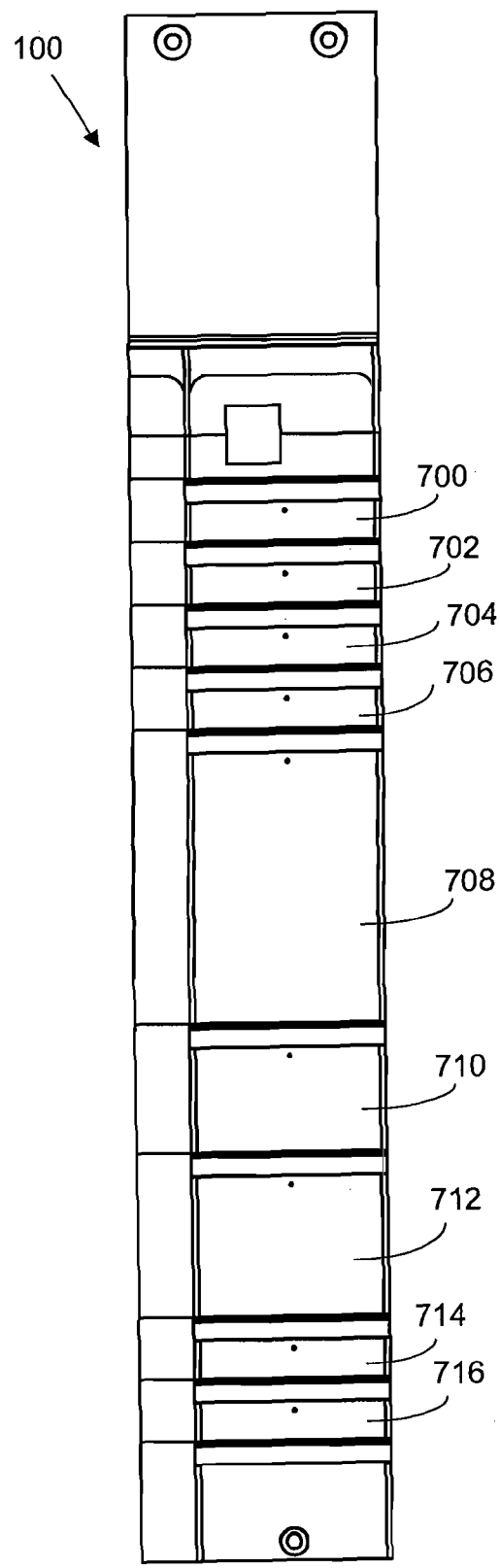
FIG. 9 is a schematic diagram of a modular platen configured to perform an H&E staining procedure on a biological sample adhered to a microscope slide.

As mentioned previously, the modular platen system illustrated in FIG. 3 can be configured to perform any type of substrate treatment procedure. In particular, where the substrate is a microscope slide carrying a biological sample (such as a tissue section or a cytology sample), the platen can be configured to perform any type of staining routine (such as primary staining, special staining, immunohistochemistry, in situ hybridization, and combinations thereof). FIG. 9 illustrates a platen 100 that can be used to perform a primary hematoxylin and eosin (H&E) staining procedure on a slide-mounted biological sample. A plurality of liquid application station/stripping element combinations of a variety of lengths are employed. For a substrate moved along the platen at a constant speed, the length of the liquid application stations determine the length of time spent on a particular station during which time the sample can be exposed to a particular liquid. In FIG. 9, which shows a top view of platen 100, a slide placed sample side down on the platen is transported past the platen segments from top to bottom in the figure by a substrate transporter. The first liquid application station encountered 700 is used to apply and remove limonene (or other de-paraffinization solution) to the sample to effectuate de-paraffinization. A second liquid application station 702 also applies and removes limonene to ensure more complete de-paraffinization. The sample is then washed twice with ethanol at stations 704 and 706. A hematoxylin dye solution is applied to the sample at station 708, which station is the longest station in this embodiment and provides an extended time during which the sample is exposed to and stained by the dye. The hematoxylin stained sample is then blued using an acidic bluing solution at station 710. The sample is then exposed to an eosin solution at station 712, followed by 2 ethanol washes at stations 714 and 716. Stripping elements (not specifically labeled) at the trailing ends of the liquid application stations help ensure minimal carryover of reagents between stations.

Figure 10:
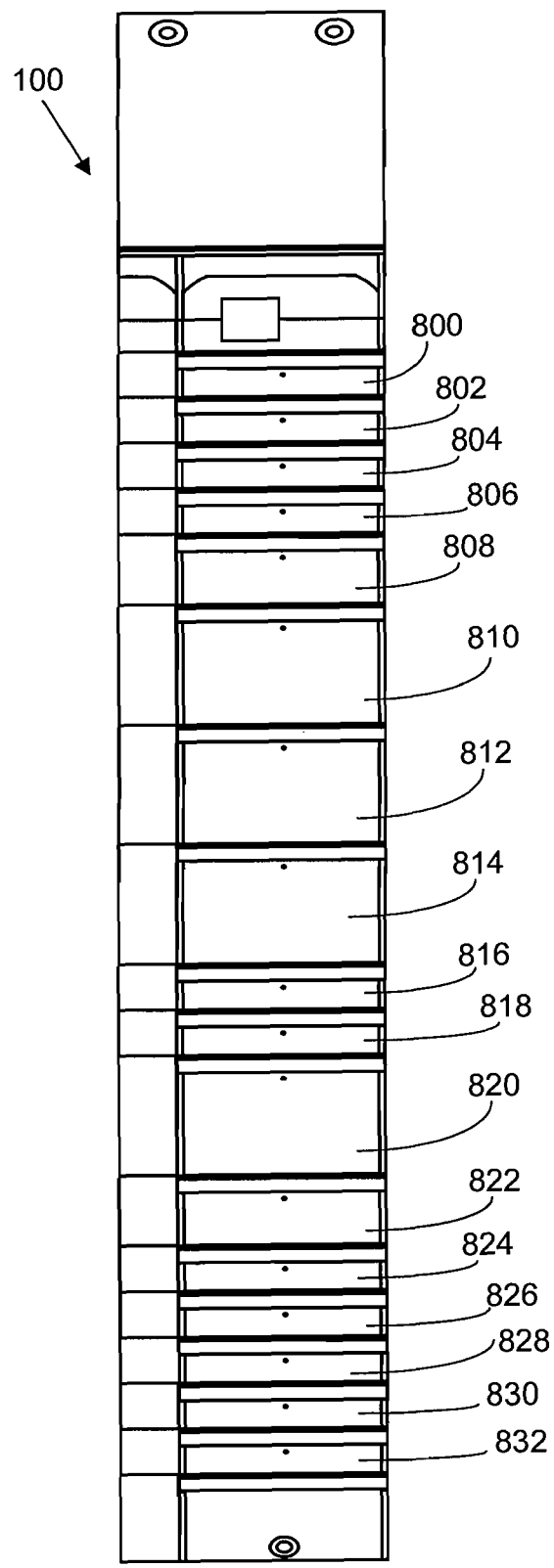
FIG. 10 is a schematic diagram of a modular platen configured to perform an immunohistochemical (IHC) procedure on a biological sample adhered to a microscope slide.

FIG. 10 shows a modular platen configured to perform a more complicated immunohistochemical (IHC) procedure on a biological sample adhered to a microscope slide. In this embodiment, platen 100 includes first de-paraffinization station 800 where the slide is contacted (on the sample side) with a de-paraffinization liquid (such as limonene, xylene, or a surfactant containing solution), and a second de-paraffinization station 802 where the slide is contacted with a second aliquot of de-paraffinization liquid. After rinsing the slide with ethanol at stations 804 and 806, the slide is contacted at station 808 with an inhibitor solution (for example, a hydrogen peroxide solution) used to reduce non-specific background staining. At station 810, a primary antibody is contacted with the slide/sample and allowed to incubate (Note: any primary antibody could be delivered in this step, for example, using a robotic dispenser to retrieve a particular antibody solution from a 96-well plate). A secondary antibody that binds to the primary antibody is contacted to the slide/sample at station 812. At station 814, a combination of antibody conjugates that specifically bind the primary and secondary antibodies is contacted to the slide/sample. The conjugates in this embodiment are conjugates of an antibody and a horseradish peroxidase (HRP) enzyme. Once antibodies that are not specifically bound are rinsed from the slide at stations 816 and 818 using a buffered wash solution, a diaminobenzidine (DAB)/hydrogen peroxide solution is contacted to the sample at station 820 and allowed to incubate, during which time the HRP enzyme of the conjugate converts the soluble DAB into an insoluble brown precipitate at the sites in the sample where the primary antibody is specifically bound. After treatment with copper at station 822 to darken the hue of the DAB precipitate, the sample is washed with buffer at station 824, followed by two rinses with ethanol at stations 826 and 828, and two rinses with limonene at stations 830 and 832 that prepare the sample for coverslipping. Stripping elements (not specifically labeled) at the trailing ends of the liquid application stations help ensure minimal carryover of reagents between stations. Of course, platens can be configured to perform other staining protocols such as ISH protocols since particular platen segments can be independently heated to perform the target retrieval and hybridization steps. Special staining protocols (such as Giemsa staining) also can be accommodated due to the versatility of the platen format.

Figure 11:
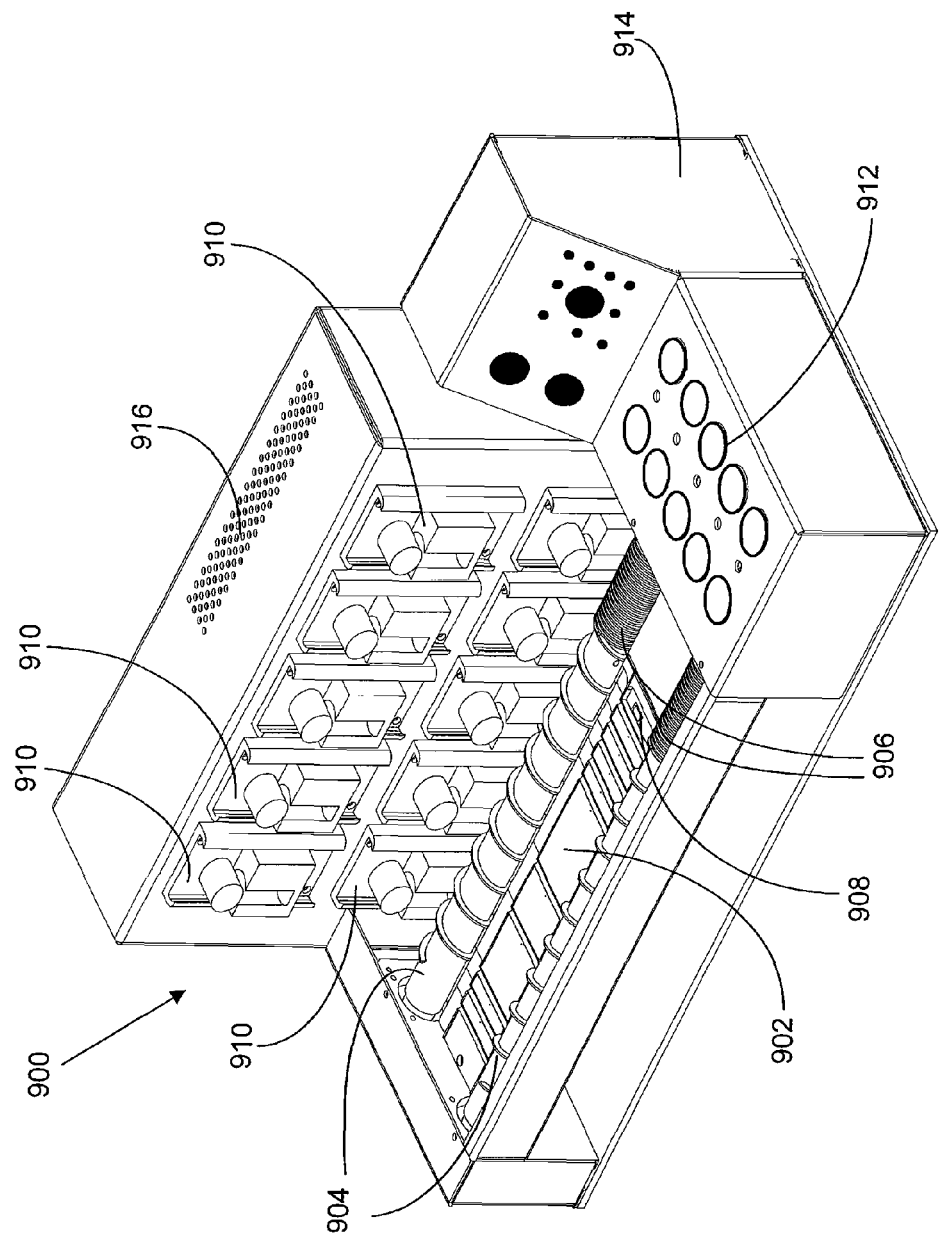
FIG. 11 is a perspective diagram of an embodiment of an apparatus for staining biological samples adhered to microscope slides.

FIG. 11 is a perspective diagram of an embodiment of an apparatus for staining biological samples adhered to microscope slides. Apparatus 900 includes configurable, modular platen 902 that includes a plurality of stripping elements. The stripping elements are located at the trailing ends of a plurality of liquid application stations of varying lengths. In this embodiment, the substrate transporter is a pair of helical screws 904 that operate together as a screw drive to convey microscope slides along platen 902 (see, for example, U.S. Pat. No. 3,431,886). Microscope slides placed on edge into the closely spaced helical elements of portions 906 of screws 904 are conveyed on edge toward the platen until they reach a slide positioning segment of the platen 908 where the helical elements of screws 904 become more widely spaced and the slide is laid sample-side down onto platen 902. A plurality of liquid applicators (unlabeled, but shown as single apertures through the platen) are used to dispense liquids to the capillary spaces between the slides and the liquid application stations of platen 902. Pumps 910 are connected to and supply liquids to the liquid applicators by pumping liquids from liquid reservoirs 912 to which they are individually connected. Control unit 914 (such as a microprocessor, microcomputer or computer) controls pumps 910 and the motion of the screw drive 904 (for example, by controlling an electric motor that turns the helical screws of the screw drive) to coordinate dispensation of liquids to the liquid application stations of platen as slides pass along platen 902. The screw drive can be operated at constant or variable speed, or stopped and started as needed to accomplish any particular staining protocol desired. Sensors or switches (not shown) also can provide signals to the control unit 914 that indicate a slide is in place over a liquid application station and ready to receive an aliquot of a liquid. Housing 916 includes a power supply, fluidic connections and electrical connections for the apparatus, and also can include a vacuum pump. Since platen 902 in this embodiment is configurable, control unit 914 can have stored in memory alternate sets of commands to enable staining protocols for use with alternate platen configurations. Or, control unit 914 can include a graphical user interface that allows a user to create a protocol for any particular staining procedure and/or platen configuration. Control unit 914 can further be connected to a large network of computers such as a Laboratory Information System (LIS) or any other type of system utilized to track patient samples and monitor workflow in a laboratory (see, for example, U.S. Patent Application Publication Nos. 2007/196909 and 2007/159982). Control unit 914 also can be configured to provide remote monitoring and trouble-shooting of the instrument.

Figure 12:
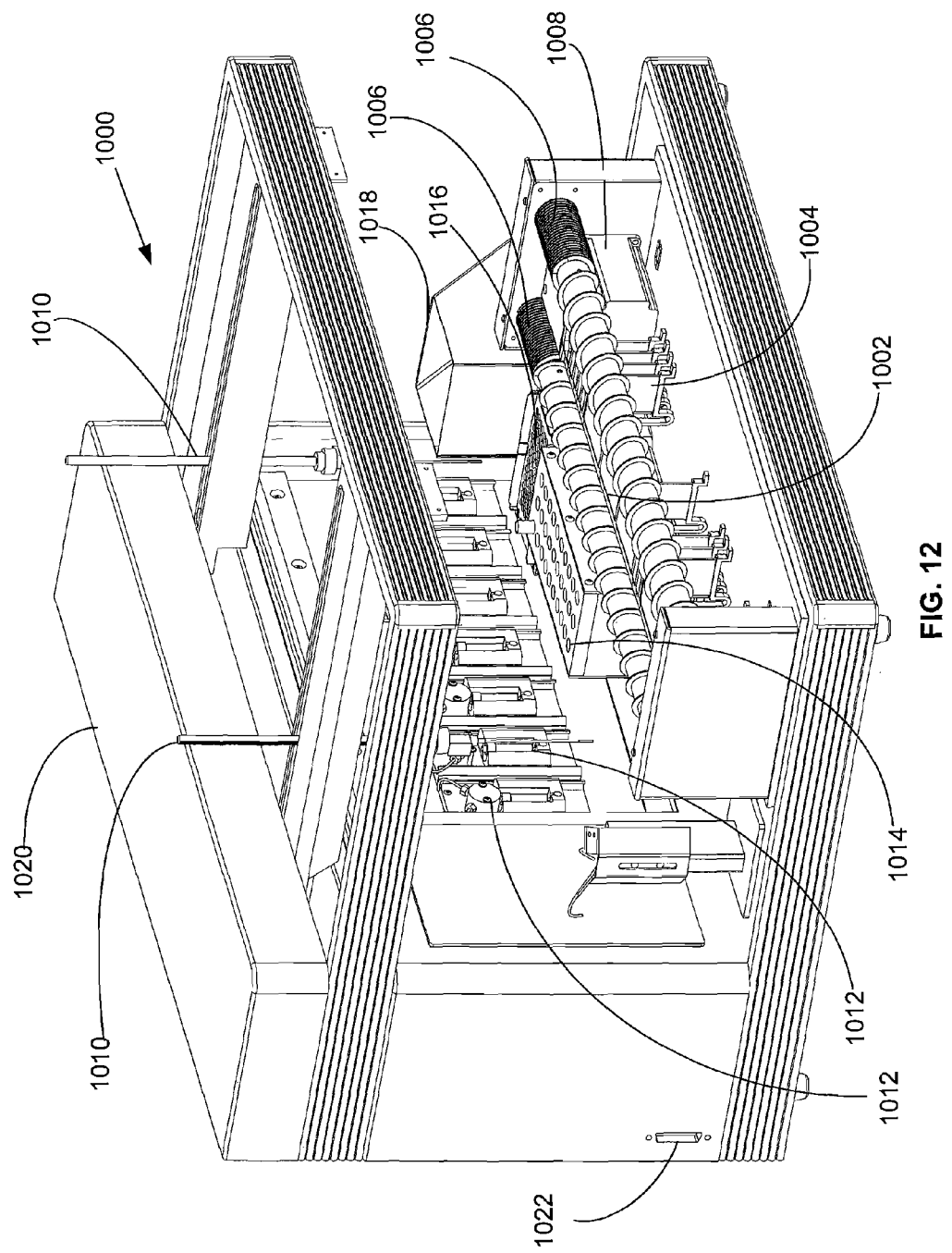
FIG. 12 is a perspective diagram of an embodiment of an apparatus that includes a robotic dispenser.

FIG. 12 is a perspective diagram of another embodiment of an apparatus according to the disclosure. Apparatus 1000 includes platen 1002, which platen includes a plurality of liquid application stations having stripping elements. In contact with the stripping elements are absorbent pads 1004. In this embodiment, helical screws 1006 (driven by electric motor 1008) act as the substrate transporter, and robotic dispensers 1010 and pumps 1012 acts the liquid applicators. Also included in this embodiment, is a multi-well plate holding reagent liquids 1014, disposable pipette tip holder 1016 and spent pipette tip holder 1018. Housing 1020 includes a power supply, bulk liquid containers connected to pumps 1012, motors for the pumps and motors for moving robotic dispensers 1010, and one or more microprocessors that control the pumps, dispensers, substrate transporter etc. and that can be connected to an external computer through port 1022 (such as a USB or RS232 port). In operation, a slide is loaded on edge into the closely placed portion of helical screws 1006 at the far end of the platen 1002. As the slide moves along the platen, it is lowered onto the platen surface sample-side down (such as tissue section down). Depending upon the purpose of a particular liquid application station, a liquid (such as a reagent solution or a solvent) is dispensed to the slide either through an aperture connected to one of pumps 1012, or through a robotic dispenser 1010. Typically, bulk liquids that are common to several procedures are provided through pump and aperture combinations, whereas reagents that are particular to a process (such as an antibody used in an IHC process, a nucleic acid probe utilized in an ISH process, or a detection reagent) are typically delivered to a particular liquid application station using one or both of the robotic dispensers. Robotic dispensers 1010 are typically programmed to retrieve a fresh pipette tip from holder 1016, to retrieve an aliquot of a reagent from multi-well plate 1014, dispense the aliquot to a liquid application station of the platen (for example, in a series of spots across the liquid application station or into a divot connected to a channel), and then eject the pipette tip into spent pipette tip holder 1018. Successive reagents are each then dispensed using fresh pipette tips to help eliminate cross-contamination that could otherwise occur if the same pipette tip were used to dispense multiple reagents. The one or more microprocessors enclosed in housing 1020 are used to control and time reagent delivery to particular slides as they are translated along the platen. Port 1022 can connect the apparatus to a microcomputer, which microcomputer can be part of a larger laboratory information management system. Although not shown in detail in FIG. 12, slides will typically be labeled with a machine readable code such as an RFID tag or a type of barcode that specifies (or refers to) a protocol to be performed on the slide. A code reader located at the beginning section of the platen will communicate this information to the controlling microprocessor(s), which microprocessor(s) will deliver reagents to particular liquid application stations in accordance with the specified protocol. If any portions or segments of the platen are to be heated or cooled during the protocol, the microprocessor(s) will also function to control the temperature of those portions.

Figure 13:
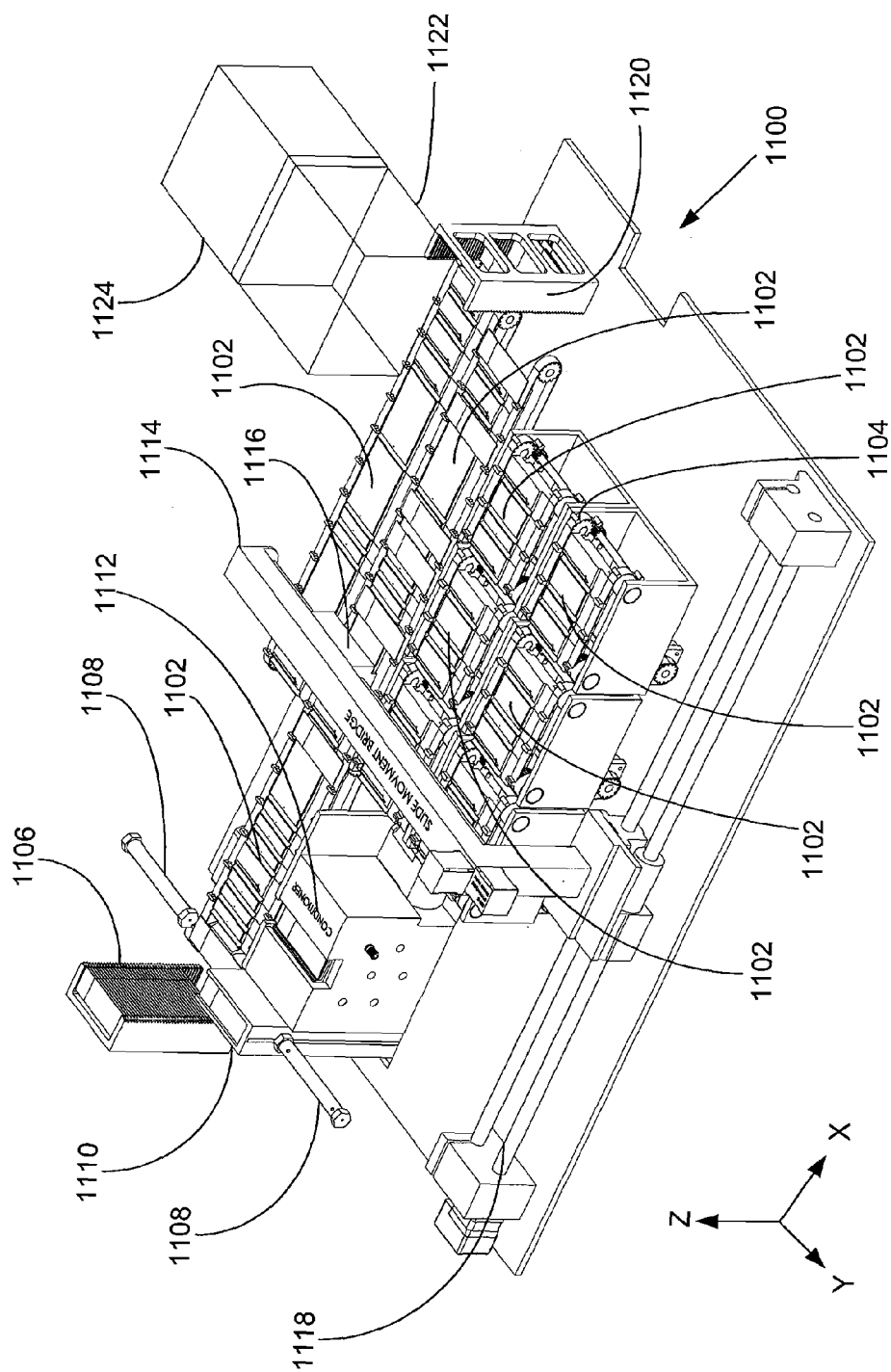
FIG. 13 is a perspective diagram illustrating a multi-platen embodiment of the disclosed apparatus.

FIG. 13 is a perspective diagram illustrating a multi-platen embodiment of the disclosed apparatus. In this embodiment, multiple small platens 1102, each having a belt drive 1104 for substrate transport along the platens (only one belt labeled for clarity of the remainder of the diagram). Substrates, in this case microscope slides labeled with a machine-readable code, are loaded label-side and sample-side down into input cassette 1106. As the slides are retrieved from the input cassette, the code on each slide is read by a code reader (not shown), and the instructions that are on the code, or are referenced by the code, are used to determine the treatments to be performed on a given slide on one or more of the platens. Slides that are not indicated to be "STAT (that is to be completed as fast as possible through priority scheduling through the apparatus)" can be pushed into and out of holding cassette 1110 by pistons 1108. Both input cassette 1106 and holding cassette 1110 can move up and down slides for input or output of slides to or from particular positions in the cassettes. Also shown in FIG. 13 is on-line sample conditioner 1112 that can receive and treat slides carrying samples that are to be stained with an IHC or ISH protocol that includes either an antigen- or target-retrieval step, respectively. Although all paraffinembedded tissue sections on slides may be similarly de-paraffinized on the same platen (for example, along the platen nearest to the sample conditioner 1112), slides that are to be stained in different manners (such as a primary stain, an IHC stain, or an ISH stain) will be routed to different platens within the apparatus. XYZ substrate transporter 1114 is used to move slides from one platen to another within the system. XYZ substrate transporter 1114 includes slide gripper 1116 that can move in the Z direction to place and remove slides from the platens, and can then move the slide in the Y direction back and forth along the arm of XYZ transporter 1114* (shown extending over several platens of the apparatus). Movement in the X-direction is accomplished by XYZ substrate transporter 1114 moving along rails 1118. Liquids can be delivered to the liquid application stations of the platens with any liquid applicator previously discussed (such as apertures, nozzles, robotic dispensers and combinations thereof). Once processing of a slide is complete, the slide is routed to output cassette 1120. Optionally, a slide can be routed to a coverslipper unit 1122 to place a coverslip over the sample and/or into imaging module 1124, that can be used to obtain images for quality control within the system (such as to alert a user that a particular reagent or set of processing parameters is not providing an appropriate amount of staining) and/or patient diagnoses.

Figure 14:
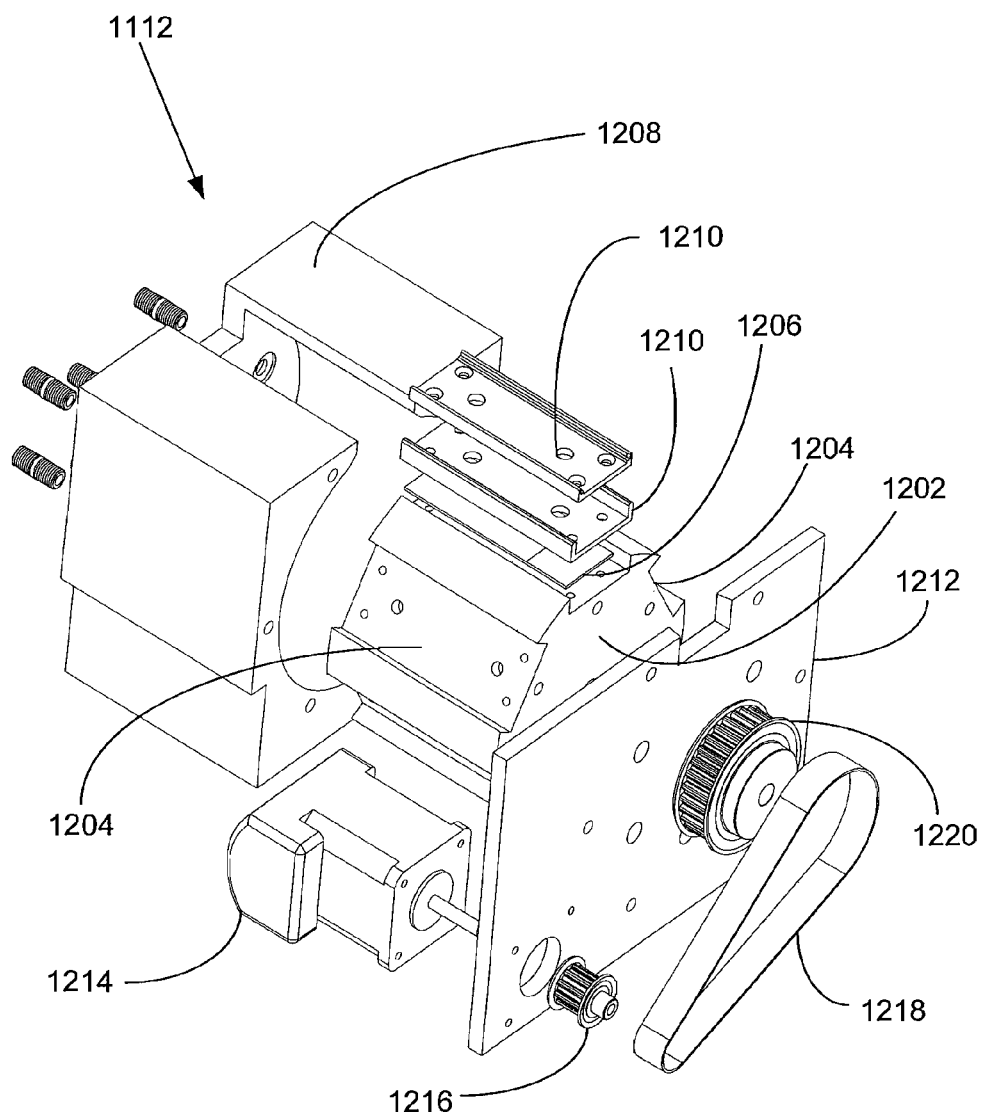
FIG. 14 is an exploded schematic diagram of a sample conditioner unit for on-line treatment of a substrate at elevated temperature and/or pressure.

FIG. 14 is an exploded schematic diagram of the sample conditioner 1112 shown in FIG. 13. Rotor 1202 having a plurality of recesses 1204 dimensioned to accommodate a substrate such as microscope slide 1206 is mounted inside of and can rotate within housing 1208. Seal members 1210 and face plate 1212 serve to seal the interior of the housing such that the substrate can be subjected to elevated temperatures and pressures as it is rotated within housing 1208 on rotor 1202. Rotor 1202 is moved within housing 1208 by electric motor 1214, which turns gear 1216, which in turn is connected through pulley 1218 to gear 1220. The amount of time that a substrate is subjected to treatment in the sample conditioner 1112 depends on the speed of electric motor 1214, and on the selected sizes of gears 1216 and 1220. A sample on a substrate can be retrieved from the conditioner after one rotation through the housing or it can remain in the conditioner for multiple rotations through the housing. The conditioner can be used for antigen retrieval or for target retrieval, and can be configured to apply heat, pressure, ultrasound, microwave energy, or any combination thereof. A solution can be held in the conditioner, and the solution can be any solution known or yet to be discovered that can facilitate antigen retrieval and/or target retrieval. Examples of solutions that can be utilized include solutions of nucleophilic agents (see, for example, U.S. Pat. No. 5,578,452) and high boiling point solvents and solutions (such as polyols like propylene glycol and ionic liquids, and solutions of such solvents containing nucleophilic agents; see, for example, U.S. Patent Application Publication No. 2005/0227298).

FIG. 15 is a perspective drawing of an embodiment of substrate treatment module incorporating a bi-directional stripping element. Module 1300 includes platen 1302, which includes a first liquid application station 1304 and a second liquid application station 1306 that are separated by bi-directional stripping element 1308. Slide drive 1310, holds an end (or ends) of a substrate such as a microscope slide. Slide drive 1310 is moved back and forth with motor 1312, and in the process carries the substrate back and forth between the first and second liquid application stations across the bidirectional stripping element 1308. Liquid applicator 1314 is, in this embodiment, a robotic pipette that can retrieve liquids from a plurality of containers (not shown) and deposit the liquids onto liquid application stations 1304 and 1306. The X, Y and Z motions of the liquid applicator 1314 are controlled by stepper motors 1316, 1318 and 1320. In operation, liquid applicator 1312 retrieves a desired first liquid from a container and places the liquid in one or more spots onto one of the liquid application stations such as first liquid application station 1304. A substrate is moved across the spots to allow the liquid to fill a capillary space between the substrate and the station, and then allowed to incubate for an amount of time. Liquid applicator 1312 is then used to retrieve and deposit a second liquid (can be the same or different as the first liquid) onto second liquid application station 1306. The substrate is then translated across bi-directional stripping element 1308 to remove the first liquid and onto the second liquid application station where the deposited second liquid then fills the capillary space between the substrate and the second liquid application station. A third liquid (same or different) can be deposited on the first liquid application station and the substrate is translated back across the bi-directional stripping element, removing the second liquid, and then allowing the deposited third liquid to contact the substrate on the first liquid application station. This process can be repeated any number of times. Any number of such substrate treatment modules can be combined to make a larger apparatus for processing substrates.

It is to be understood that the disclosed invention is not limited to the particular embodiments illustrated above and that many changes may be made without departing from the true scope and spirit of the invention, which is defined by the claims that follow. For example, any type of staining protocol or any type of substrate processing (such as preparation of SELDI chips or processing of microarrays) can be accomplished with the disclosed instruments. Also, any configuration of multiple platens can be utilized in an instrument (for example, a plurality of platens can be stacked vertically, or in a tribune configuration). Furthermore, those skilled in the art to which the invention pertains will recognize, or be able to ascertain many equivalents to the embodiments described herein. Such equivalents are intended to fall within the scope of the claims.

We claim:

1. An apparatus for applying a liquid to a substantially flat substrate, comprising:
 a substrate transporter;
 a liquid applicator; and
 a platen including a liquid application station for contacting a liquid to a surface of the substrate and including a capillary space formed between the substrate and the liquid application station,
 wherein the platen further comprising a stripping element for removing liquid at an end of the liquid application station, and
 wherein the stripping element includes an intersecting gap intersecting the capillary space between the substrate and the liquid application station and extending at least partially through the thickness of the platen to accomplish removal of liquid, and
 wherein movement of the substrate relative to the stripping element reduces the capillary space and removes liquid, and
 wherein the stripping element further includes an air barrier.

2. The apparatus of claim 1, wherein the substrate transporter comprises one or more of a belt drive, a screw drive, a chain drive, and a slide drive.

3. The apparatus of claim 1, wherein the liquid applicator comprises one or more of an aperture through the platen, a stationary or moveable nozzle, and a robotic dispenser under microprocessor control.

4. The apparatus of claim 1, wherein the liquid application station further includes a fluid phase trap.

5. The apparatus of claim 4, wherein the fluid phase trap comprises a channel in a surface of the liquid application station.

6. The apparatus of claim 5, further comprising a divot at a trailing edge of the channel.

7. The apparatus of claim 1, wherein the platen comprises a plurality of platen segments.

8. The apparatus of claim 7, wherein the intersecting gap of the stripping element is formed at a junction between a pair of platen segments.

9. The apparatus of claim 1, wherein the platen includes a spacer that holds the substrate apart from the liquid application station to form a capillary space between the substrate and the liquid application station.

10. The apparatus of claim 9, wherein the spacer comprises a pair of rails along opposite edges of the liquid application station that are aligned with a direction of motion of the substrate across the platen, which motion is imparted to the substrate by the substrate transporter.

11. The apparatus of claim 1, wherein the intersecting gap of the stripping element comprises a capillary gap that intersects the capillary space between the substrate and the liquid application station, and a force exerted on the liquid through the intersecting gap comprises a capillary force.

12. The apparatus of claim 1, wherein a force exerted on the liquid through the intersecting gap comprises a vacuum created in the gap.

13. The apparatus of claim 1, further comprising a wicking member in contact with the platen.

14. The apparatus of claim 1, wherein the intersecting gap and the air barrier are separated by less than about 0.080 inches.

15. The apparatus of claim 1, wherein the platen comprises a plurality of coplanar liquid application stations.

16. The apparatus of claim 1, wherein the stripping element removes substantially all of the liquid applied to the substrate on the liquid application station.

17. The apparatus of claim 1, comprising a plurality of liquid application stations and associated stripping elements, wherein waste liquids from two or more stripping elements are separated.

18. The apparatus of claim 17, wherein two or more stripping elements are in contact with different wicking members, thereby segregating waste from the two or more stripping elements.

19. The apparatus of claim 1, wherein the liquid application station includes a heater.

20. The apparatus of claim 1, wherein the platen includes two or more liquid application stations each having independently controlled heaters.

21. The apparatus of claim 1, wherein at least a portion of the platen is treated to with a liquid-repelling substance to reduce adhesion of the liquid to the surface of the platen.

22. The apparatus of claim 21, wherein the liquid comprises a polar liquid and the platen is treated with a hydrophobic substance.

23. The apparatus of claim 1, wherein the stripping element comprises a bi-directional stripping element.

24. The apparatus of claim 1, wherein the platen includes at least one segmented liquid application station.

25. The apparatus of claim 1, wherein the apparatus includes a plurality of platens.

\* \* \* \* \*